United States Patent
Wikelski et al.

(10) Patent No.: US 10,877,179 B2
(45) Date of Patent: *Dec. 29, 2020

(54) DISASTER ALERT MEDIATION USING NATURE

(71) Applicant: MAX-PLANCK-GESELLSCHAFT ZUR FOERDERUNG DER WISSENSCHAFTEN E.V., Munich (DE)

(72) Inventors: Martin Wikelski, Constance (DE); Uschi Müller, Constance (DE); Wolfgang Arne Heidrich, Wörthsee (DE); Franz Xaver Kümmeth, Munich (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/394,432

(22) Filed: Apr. 25, 2019

(65) Prior Publication Data

US 2019/0265388 A1 Aug. 29, 2019

Related U.S. Application Data

(63) Continuation of application No. 14/397,876, filed as application No. PCT/EP2013/059606 on May 8, 2013, now Pat. No. 10,310,140.

(30) Foreign Application Priority Data

May 8, 2012 (EP) .................................. 12167197

(51) Int. Cl.
*G01W 1/10* (2006.01)
*G01V 1/00* (2006.01)
(Continued)

(52) U.S. Cl.
CPC .......... *G01W 1/10* (2013.01); *A61B 5/02055* (2013.01); *A61B 5/0476* (2013.01); *A61B 5/16* (2013.01);
(Continued)

(58) Field of Classification Search
CPC ..... A61B 5/02055; A61B 5/0476; A61B 5/42; G01V 1/008; G01W 1/10; G06Q 50/265
See application file for complete search history.

(56) References Cited

U.S. PATENT DOCUMENTS

| 2004/0061606 A1 | 4/2004 | Gronvold |
| 2007/0204804 A1* | 9/2007 | Swanson .............. A01K 15/023 119/721 |

(Continued)

FOREIGN PATENT DOCUMENTS

| CN | 101221248 A | 7/2008 |
| EP | 2 284 576 A1 | 2/2011 |
| WO | 2009/004804 A1 | 1/2009 |

OTHER PUBLICATIONS

Wikipedia, Very high frequency, Jul. 12, 2011 (Year: 2011).*

(Continued)

*Primary Examiner* — Kyle R Quigley
(74) *Attorney, Agent, or Firm* — Sughrue Mion, PLLC

(57) ABSTRACT

A method for forecasting an environmental event/a type of environmental event includes acquiring at least one test data set of at least one behavioural and/or physiological parameter of a population of animals; generating a test profile based on said at least one test data set, representing behaviour and/or physiological status of the population of animals; calculating a ratio between the test profile and a first reference profile; and setting an alert, if said ratio reaches a predefined threshold value.

28 Claims, 16 Drawing Sheets

(51) Int. Cl.
  *A61B 5/16*    (2006.01)
  *A61B 5/0205*  (2006.01)
  *A61B 5/0476*  (2006.01)
  *A61B 5/00*    (2006.01)
  *G06Q 50/26*   (2012.01)

(52) U.S. Cl.
  CPC ............... *A61B 5/42* (2013.01); *G01V 1/008* (2013.01); *G06Q 50/265* (2013.01)

(56) References Cited

U.S. PATENT DOCUMENTS

| 2007/0214886 A1* | 9/2007 | Sheynblat ............... G01P 15/18 73/509 |
| 2010/0302004 A1 | 12/2010 | Winstead et al. |
| 2012/0123983 A1 | 5/2012 | Flexer et al. |

OTHER PUBLICATIONS

Joseph L. Kirschvink, "Earthquake Prediction by Animals: Evolution and Sensory Perception", Bulletin of the Seimological Society of America, Apr. 2000, pp. 312-323, vol. 90, No. 2.
Communication dated Jun. 19, 2017, from the European Patent Office in counterpart European Application No. 13727061.7.
Communication dated May 22, 2018 issued by the European Patent Office in counterpart European application No. 13727061.7.
R.A. Grant, et al., "Predicting the unpredictable; evidence of pre-seismic anticipatory behaviour in the common toad", Journal of Zoology, 2010, pp. 263-271, vol. 281.
A. Ya. Sidorin et al. "Biological Indicators in Studies of Earthquake Precursors" Geophysical Research Abstracts vol. 14, EGU2012-6268: Apr. 22, 2012 (1 page total).
International Search Report for PCT/EP2013/059606, dated Mar. 18, 2014.
Written Opinion for PCT/EP2013/059606, dated Mar. 18, 2014.
Bhargava et al.. Earthquake Prediction through Animal Behavior A Review, Indian Journal of Biomechanics, Mar. 2009.
Deschpande, Earthquakes, Animals and Man Chapter III Animal Response to Earthquakes, Proc. Indian natn. Sci. Acad., 1986.
Kenagy et al., Animal behavior as a predictor of earthquakes an analysis of rodent activity rhythms, Z. Tierpsychol., 52, 269-284, 1980.
Tong, Abnormal Animal Behavior and the Prediction of Earthquakes, Northeastern Illinois University, Aug. 1988.

* cited by examiner

FIG. 11
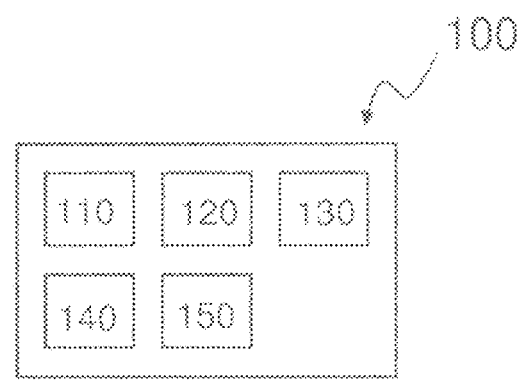
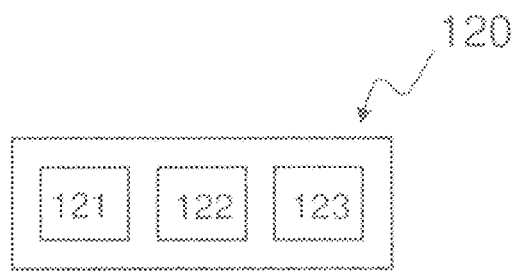

DISASTER ALERT MEDIATION USING NATURE

CROSS REFERENCE TO RELATED APPLICATIONS

This is a continuation of U.S. application Ser. No. 14/397,876 filed Oct. 30, 2014 which is a National Stage of International Application No. PCT/EP2013/059606, filed May 8, 2013, claiming priority based on European Patent Application No. 12167197.8, filed May 8, 2012, the contents of all of which are herein incorporated by reference in their entireties.

BACKGROUND

The present invention relates to a method for forecasting an environmental event/a type of environmental event comprising the steps of: acquiring at least one test data set of at least one behavioural and/or physiological parameter of a population of animals; generating a test profile based on said at least one test data set, representing behaviour and/or physiological status of the population of animals; calculating a ratio between the test profile and a first reference profile; and setting an alert, if said ratio reaches a predefined threshold value. The present invention further relates to a system for forecasting an environmental event/a type of environmental event comprising at least one data acquisition unit configured to acquire at least one data set of at least one behavioural and/or physiological parameter of a population of animals; at least one profile generation unit configured to generate at least one first reference profile and/or at least one test profile wherein each profile is based on at least one data set; at least one ratio calculation unit configured to calculate at least one ratio between the at least one test profile and one of the at least one first reference profile; at least one alert unit configured to raise an alert if at least one of the at least one calculated ratio reaches a predefined threshold value. The present invention also relates to a computer program product comprising one or more computer readable media having computer executable instructions for performing the steps of the method for forecasting an environmental event/a type of environmental event.

Natural disasters are notoriously difficult to predict. For example, earthquakes are a sudden phenomenon. Seismologists are unable to predict them precisely in time and space. However, their impact is considerable. An estimated 500,000 detectable quakes occur in the world each year. Of those, 100,000 can be felt by humans, and 100 cause damage. Similarly, tsunamis and volcanic eruptions cause considerable damage.

The magma chamber of Mt. Etna rests very high above the surface at ca. 1000 meters, causing frequent gas releases including $SO_2$ and $H_2S$ that are potentially linked to smaller and larger eruptions.

Since the year 1600 A.D., there have been at least 60 flank eruptions and many summit eruptions. Nearly half of the eruptions have occurred since the start of the 20th century. Since the year 2000 there have been five flank eruptions of Etna, in 2001, 2002-2003, 2004-2005, 2007 and 2008. Other major 20th-century eruptions occurred in 1949, 1971, 1981, 1983 and 1991-1993.

From Oct. 23, 2011 until Apr. 5, 2012, there have been 10 discernable volcanic events. Five of these events include paroxysmal explosions (paroxysmal events Nr. 19 to 23). Two of the paroxysmal events were major events, with volcanic lava and ash thrown high into the atmosphere (Volcanic Explosivity Index (VEI) of 2).

Whenever a natural disaster strikes, people anecdotally report that 'animals knew it beforehand'. Examples include domestic dogs, zoo animals or elephants screaming and running ahead of earthquakes or tsunamis. Thus far, only few inconclusive post-hoc analyses have been conducted on animals accidentally observed before and during natural disasters, thus not allowing for predictive capabilities.

These post-hoc reports of unusual behavior of animals preceding catastrophes have been made since centuries. For example, as early as in 373 B.C., historians recorded that animals, including rats, snakes and weasels, deserted the Greek city of Helice just days before a quake devastated the place. Since then, other post-hoc accounts of animals anticipating earthquakes have continued to surface across the centuries. Catfish moving violently, chickens that stop laying eggs and bees leaving their hive in a panic have been reported. Countless pet owners claimed to have witnessed their individual cats and dogs acting strangely before the ground shook, barking or whining for no apparent reason, or showing signs of nervousness and restlessness.

There have been examples where authorities successfully forecast a major earthquake, based in part on the observation of the unusual behavior of animals. Based on the observation of animals in 1975, Chinese officials ordered the evacuation of Haicheng, a city with one million inhabitants, just days prior to a 7.3-magnitude quake. Only a small portion of the population was hurt or killed. If the city had not been evacuated, it is estimated that the number of fatalities and injuries could have exceeded 150,000. The Haicheng incident provides perhaps the best anecdotal evidence that earthquakes might be predictable through the direct observation of animals. However, in this context no predefined parameters were analyzed. The "unusual behavior" of the animals has been observed by chance and has been accidently interpreted as a hint for an event, what, however, could only be verified by retrospective considerations.

Before giant tsunami waves slammed into Sri Lanka and India coastlines in recent years, wild and domestic animals seemed to know what was about to happen and fled to safety. It has been widely reported in newspapers, but not scientifically evaluated or proven, that elephants screamed and ran for higher ground, dogs refused to go outdoors, flamingos abandoned their low-lying breeding areas, and zoo animals rushed into their shelters and could not be enticed to come back out.

Possible mechanistic explanations for the high sensitivity of wildlife to natural disasters are that animals have a more acute integration of hearing, smell and other senses that might enable them to hear or feel the Earth's vibration.

Currently, there exists no systematic observation of animals with respect to their ability to forecast natural changes and/or disasters. The only studies conducted thus far are retrospective (i.e. post-hoc) analyses. Accordingly, in these post-hoc or and hind-sight analyses, animals were observed by chance "doing something strange" before an environmental change happened (see Fujimoto, 2008, Primates 49:73-76 and Grant, 2010, Journal of Zoology 281:263-271). These publications use post-hoc explanations for "strange" animal behaviour that could be related to singular events of environmental change.

After the environmental change, researchers or animal keepers interpreted the behaviour of animals in the light of the environment event (e.g., toads unexpectedly left ponds in Italy a few days before a major earthquake happened).

Generally, researchers in animal behaviour use bio-logging devices to study the behaviour of animals in the wild. Such devices include radio transmitters, GPS loggers and 3D-acceleration loggers.

Wild organisms were shown to exhibit high sensitivity towards environmental changes. Such changes can be abiotic, e.g. including climate, or biotic, e.g. including human disturbance. In the last years the physiological monitoring of wild animals (e.g., via the remote observations of heart rate) as well as the behavioural monitoring per se (e.g., the observation of individual changes in posture or location) have been advanced (see Kays, 2011, Computer J, in press; Kays, 2011, Acta Oecologica, in press, doi:10.1016/j.actao.2011.06.007; Holland, 2009, PLoS ONE 4: e8264; Bisson, 2008, Proc Roy Soc Lond B 276: 961-969; Bisson, 2011, Animal Conservation 2011: 1-8; Rattenborg, 2008, Biol Letters 4: 402-405; Cochran, 2005, Individual migratory tactics of New World Catharus thrushes: current knowledge and future tracking options from space. In: Birds of Two Worlds: Ecology and Evolution of Migration (Ed. by R. Greenberg and P. Marra), pp. 274-289. Baltimore: Johns Hopkins University Press; Wikelski, 2007, J Exp Bio 210; 181-186).

SUMMARY

A system that offers any improvement in the predictive capabilities in natural disaster warning could save human life and property and ameliorate global suffering. Thus, the technical problem underlying the present invention is the provision of novel means and methods for forecasting environmental events.

The technical problem is solved by the means and methods provided and described herein and characterized in the appended claims.

According to the invention, a method is provided for forecasting an environmental event/a type of environmental event comprising the steps of: acquiring at least one test data set of the at least one behavioural and/or physiological parameter of a population of animals; generating a test profile based on said at least one test data set, representing behaviour and/or physiological status of the population of animals; calculating a ratio between the test profile and a first reference profile; and setting an alert, if said ratio reaches a predefined threshold value.

BRIEF DESCRIPTION OF THE DRAWINGS

These and/or other aspects will become apparent and more readily appreciated from the following description of the embodiments, taken in conjunction with the accompanying drawing, in which:

FIG. 11 is a diagram illustrating a data acquisition unit and a sensor unit;

DETAILED DESCRIPTION

Figure 1:
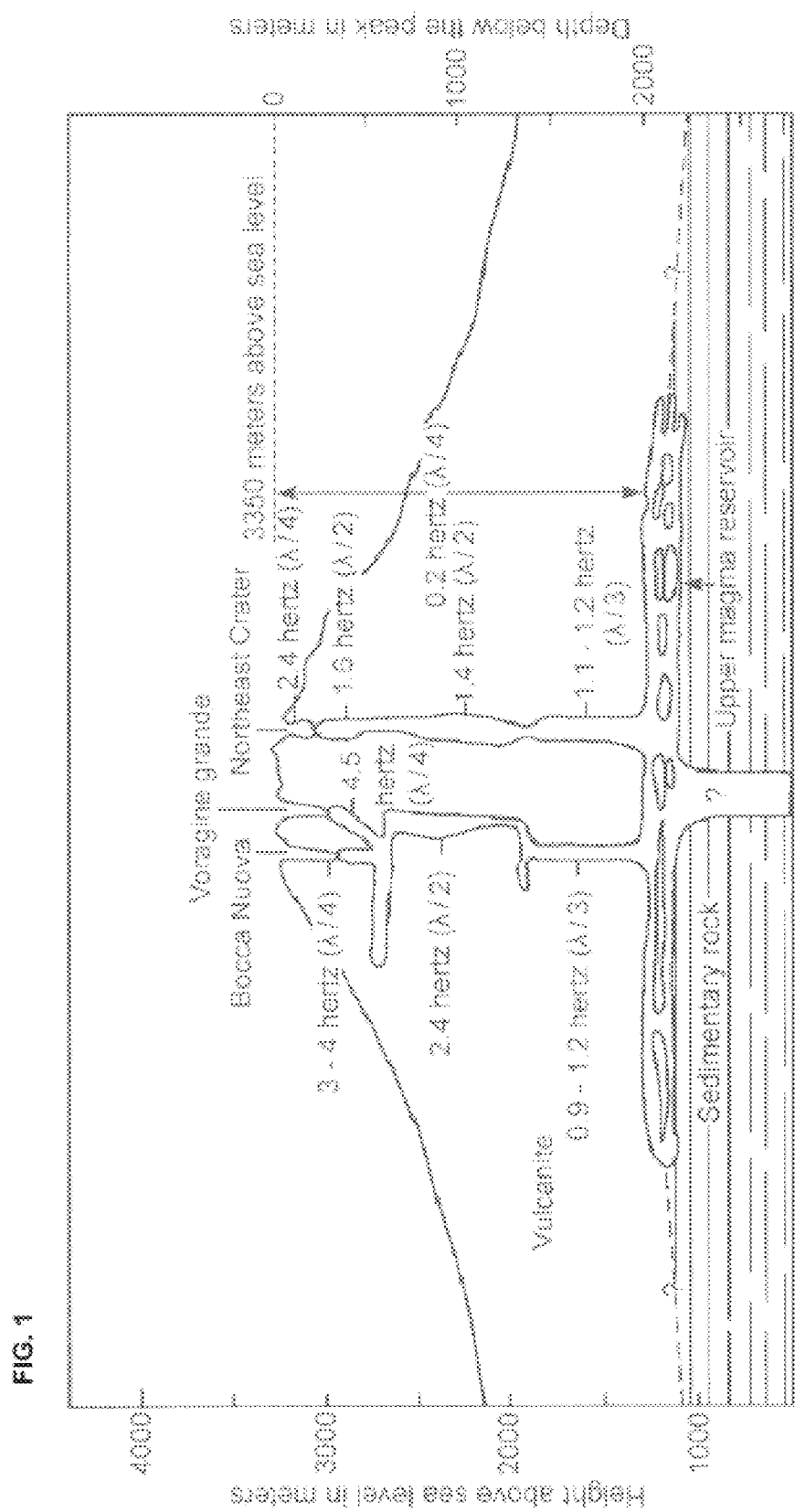
FIG. 1 shows a schematic overview of magma within Mt. Etna, Sicily.

Below, some example embodiments will be described in detail and clearly with reference to the accompanying drawings such that those skilled in the art can easily implement the disclosure.

Animal behaviour scientists have been using bio-logging devices, such as (inter alia) radio transmitters, GPS loggers and/or 3D-acceleration loggers to study behaviour of animals. However, such devices have never been used to forecast environmental events, such as volcanic events, earthquakes and the like.

The use of bio-logging devices, like radio transmitters, GPS loggers and/or 3D-acceleration loggers on animals in potential disaster areas with the aim to study and particularly to anticipate environmental or other disasters has never been conducted at any level or scale globally.

As shown in the appended examples, such devices have successfully been employed in context of the invention, i.e. in methods for forecasting (an) environmental event(s), in particular (a) volcanic event(s).

As also documented in the appended examples, the present invention, in one embodiment, provides for a method for forecasting an environmental event/a type of environmental event (e.g. a volcanic event, such as a major volcanic event) comprising the steps of: acquiring at least one test data set (e.g. global positioning points or 3D-acceleration values) of the at least one behavioural (e.g. unidirectional movement or activity) and/or physiological parameter (e.g. heart beat, temperature or blood pressure) of a population (e.g. eight individuals) of animals (e.g. goats); generating a test profile (e.g. unidirectional movement or activity over 5 days/nights or during the night) based on said at least one test data set, representing behaviour and/or physiological status of the population of animals; calculating a ratio between the test profile and a first reference profile (e.g. one instant value of the test profile compared to the average of the reference profile); and setting an alert, if said ratio reaches a predefined threshold value (e.g. a factor of 2 or 1.3).

The forecasted environmental event may be selected from the group consisting of a volcanic event, an earthquake, a marine earthquake, and a tsunami. Also any combination thereof, e.g. a marine earthquake in combination with a tsunami, etc. may be forecasted by the method(s) provided herein. In one embodiment of the invention, the forecasted environmental event is an earthquake, preferably, an earthquake having a seismic activity higher than 4, preferably higher than 5 on the Richter magnitude scale. The Richter magnitude scale is commonly known in the art and described, e.g., in Yonavjak L, Schoch R M, McKinney M L; Environmental Science: Systems and Solutions; Jones & Bartlett Pub (ma); 2007. The Richter magnitude scale (or Richter scale) is a logarithmic scale so that every unit corresponds to a 10-fold increase in the amplitude of the seismic waves. Theoretically, the Richter scale has no upper limit, but some of the largest recorded earthquakes have been ranked at about 8.9 to 9.0 (id.). According to an embodiment of the invention, the type of forecasted environmental event is a volcanic event with a Volcanic Explosivity Index (VEI) of at least 2 (i.e. a major volcanic event). In this respect it is mentioned that a minor volcanic event (VEI of 1) may not be forecasted by the inventive method. In an example of the invention, the type of forecasted environmental event is an earthquake or marine earthquake.

In one particular embodiment of the invention, the type of forecasted environmental event is a volcanic event wherein a minor earthquake (i.e. seismic activity below about 4 to 5 on the Richter magnitude scale) does not lead to an alert. The fact that minor earthquakes do preferably not lead to an alert can be advantageous since thereby false-positive alerts are prevented.

The at least one first data set of at least one behavioural and/or physiological parameter of a population of animals in the absence of the type of environmental event can comprise a plurality of data points acquired in an instant or in a predefined time interval. For example, the position of each animal of the population of animals, representing the movement of the animal, can be acquired every 30 minutes for 10 days, leaving to a sub-data set of 480 points for each animal. The sub-data sets of each animal of the population can be combined to a joint data set.

According to one embodiment of the invention, the method for forecasting a type of environmental event further comprises the steps of: acquiring at least one first data set of the at least one behavioural and/or physiological parameter of a population of animals in the absence of the environmental event/type of environmental event; generating the first reference profile based on said at least one first data set, representing normal behaviour and/or physiological status of the population of animals. The first reference profile of at least one behavioural and/or physiological parameter can be generated by summarizing the sub-data sets of each animal corresponding to the at least one behavioural and/or physiological parameter and/or the data sets or sub-data sets can comprise time-dependent data points and/or can comprise unambiguous time stamps. The corresponding data sets can also be smoothed with a filter function, e.g. a Fast-Fourier-Transform-filter or a percentile-filter.

The at least one test data set of at least one behavioural and/or physiological parameter of said population of animals can be acquired in the same manner as the at least one first data set. The at least one test data set can be acquired in the presence or the absence of the type of environmental event. The test data set can be acquired over different periods of time comprising long periods and short periods, such as hours, days, weeks, month, years, decades, or centuries. Accordingly, the test data set can comprise periods in the presence or the absence of the type of environmental event.

The test profile based on said at least one test data set can be generated in the same manner as the first reference profile, e.g. by summarizing the sub-data sets of each animal corresponding to the at least one behavioural and/or physiological parameter and/or the data sets or sub-data sets can comprise time-dependent data points and/or can comprise unambiguous time stamps.

The threshold value for raising an alert can be determined by comparing the first reference profile and the test profile as provided in the following.

Figure 7A:
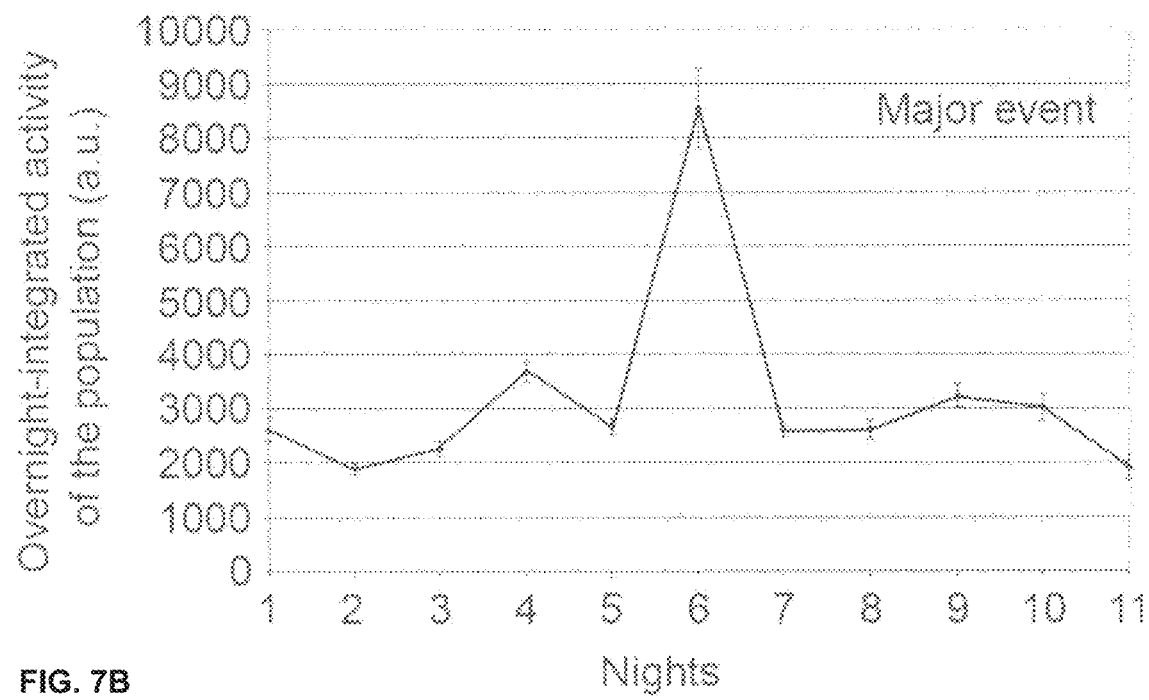
FIGS. 7A-7D show nocturnal activity of 8 goats around the $21^{st}$ and $22^{nd}$ paroxysmal events.
Figure 7B:
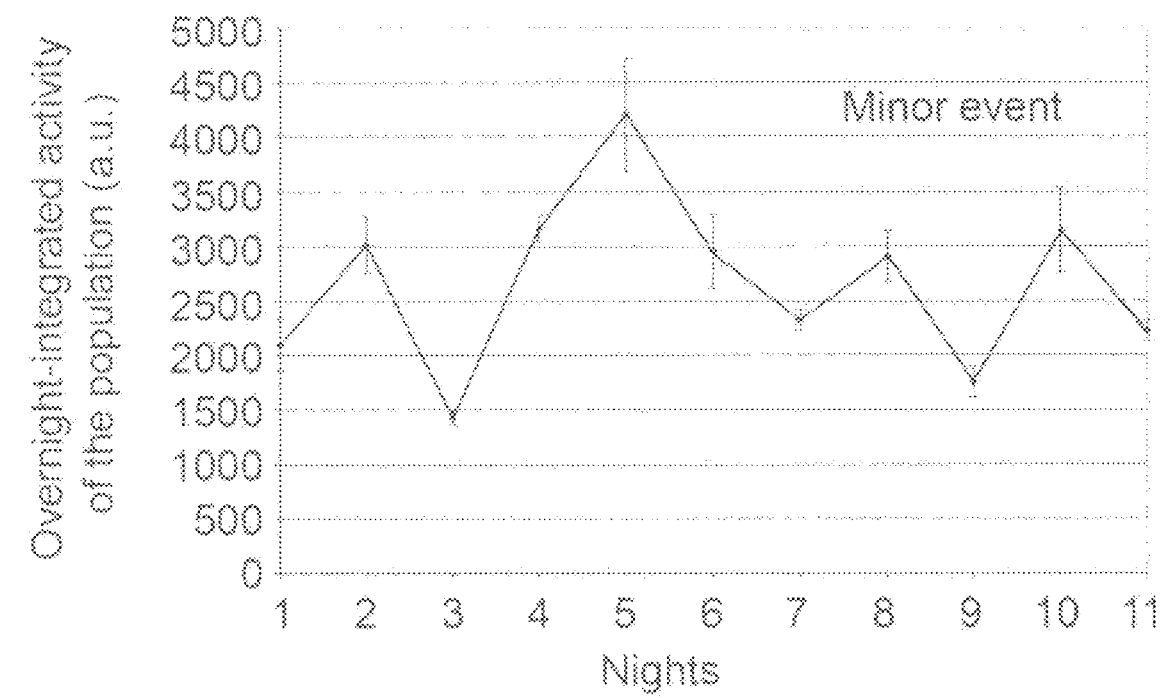

According to an embodiment of the invention, the nocturnal 3D-acceleration activity of each animal of the population can be acquired for a predefined number of nights, e.g. 5 nights for generating the reference profile. In this context, the activity of each animal can be integrated over the whole night, i.e. from 20:00 h local time to 6:00 h local time, and the overnight-integrated activities of one night of each animal of the population can be added. Repeating this step for every measured night, a reference profile can be generated which gives the summated overnight-integrated activity of the population as a function of nights (cf. FIGS. 7A and B). For the predefined number of nights of the reference profile, an average value of the summated overnight-integrated activity of the population can be calculated using standard mathematical calculations.

The threshold value can be the double average value of the summated overnight-integrated activity of the population. Accordingly, the test profile can be generated in the same manner: the activity of each animal can be integrated over the whole night and the overnight-integrated activities of the test night of each animal of the population are added. Thus the alert can be set, if the ratio between the test profile and the reference profile is 2, according to the aforementioned threshold.

Figure 7C:
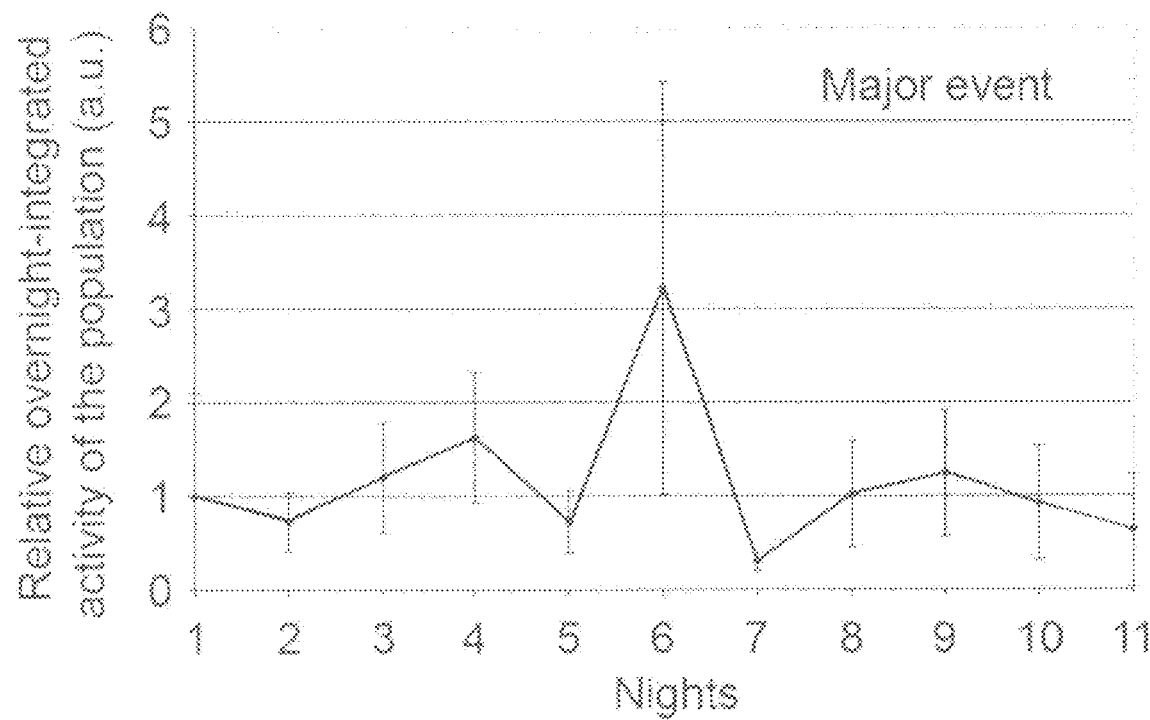
Figure 7D:
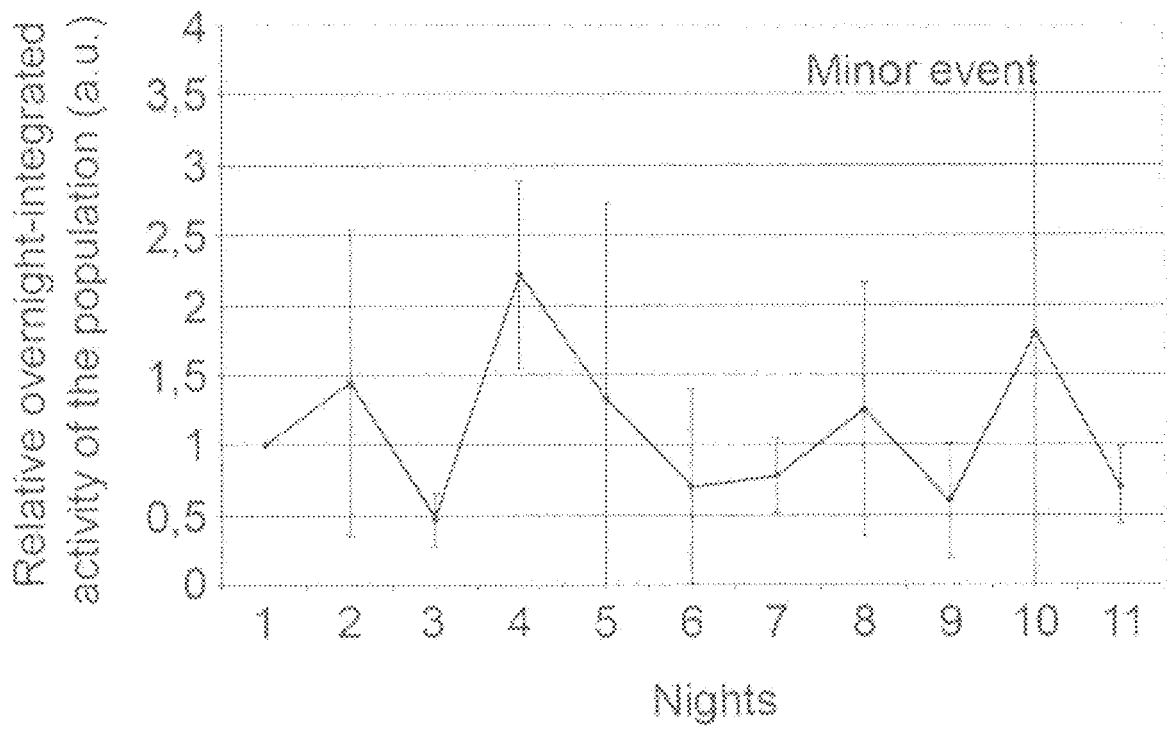

According to another embodiment of the invention, the overnight-integrated activity of each animal of the population can be considered in view of the preceding night for generating a reference profile (cf. FIGS. 7C and D). Consequently the overnight-integrated activity of each animal of the population of the first night of the reference profile is normalized to 1. Accordingly, the overnight-integrated activity of each animal of the population of the following night deviates from the one of the first night by a certain factor. Then the average of all factors of all corresponding animals of the population can be calculated to an overall factor of the population with respect to the preceding day. Repeating this step for every measured night, a reference profile can be generated which gives the relative averaged overnight-integrated activity of the population in view of the corresponding preceding night in percent as a function of nights (cf. FIGS. 7C and D).

According to an embodiment of the invention, the nocturnal 3D-acceleration activity of each animal of the population can be acquired in one night, e.g. in steps of two minutes. Then, the 3D-acceleration activity can be summated for each animal of the population for every acquired instant of time and can be divided by the number of animals in the population resulting in an average of 3D-acceleration activity per acquired instant of time (i.e. the 3D-acceleration activity can be averaged). The averaged 3D-acceleration activity can be further averaged for every 30 minutes starting from the first measured instant. Afterwards, the 3D-acceleration activity, which can be averaged in population and in time can be subsequently summated, i.e. after 60 minutes the 3D-acceleration activity averaged in population and in time of the first 30 minutes and the second 30 minutes can be summated, after 90 minutes, the 3D-acceleration activity averaged in population and in time of the first 30 minutes, the second 30 and the third 30 minutes can be summated resulting in an accumulation of measured 3D-acceleration activity values. This recursive function is set forth until the 3D-acceleration activity of the last 30 minutes of the measured night. Thus, the reference profile is generated, representing the accumulated averaged 3D-acceleration activity of the population during one night.

The test profile can be generated in the same manner representing the accumulated averaged 3D-acceleration activity of the population during one night. As soon as the value of the 3D-acceleration activity averaged in population and for 30 minutes of the test profile reaches a value which is 1.3 of the corresponding value of the reference profile, the alert can be set (cf acceleration curve of FIG. 8).

According to an embodiment of the invention, diurnal unidirectional movement of a population can be used for generating the test profile and the reference profile. Therefore, the unidirectional movement of each animal of the population can be acquired by the GPS module for a predefined number of days, e.g. 5 days, as a reference profile. In this context, the unidirectional movement of each animal can be integrated over the whole day, i.e. from 6:00 h local time to 20:00 h local time, and the daytime-integrated unidirectional movement of one day of each animal of the population can be added. Repeating this step for every measured day, a reference profile can be generated which gives the summated daytime-integrated unidirectional movement of the population as a function of nights (cf. FIG. 9A). For the predefined number of days of the reference profile, an average value of the summated daytime-integrated unidirectional movement of the population can be calculated.

The threshold value can be the double average value of the summated daytime-integrated unidirectional movement of the population. Accordingly, the test profile can be generated in the same manner: the unidirectional movement of each animal can be integrated over the whole day and daytime-integrated unidirectional movements of the test night of each animal of the population are added. Thus the alert can be set, if the ratio between the test profile and the reference profile is 2, according to the aforementioned threshold.

Figure 9A:
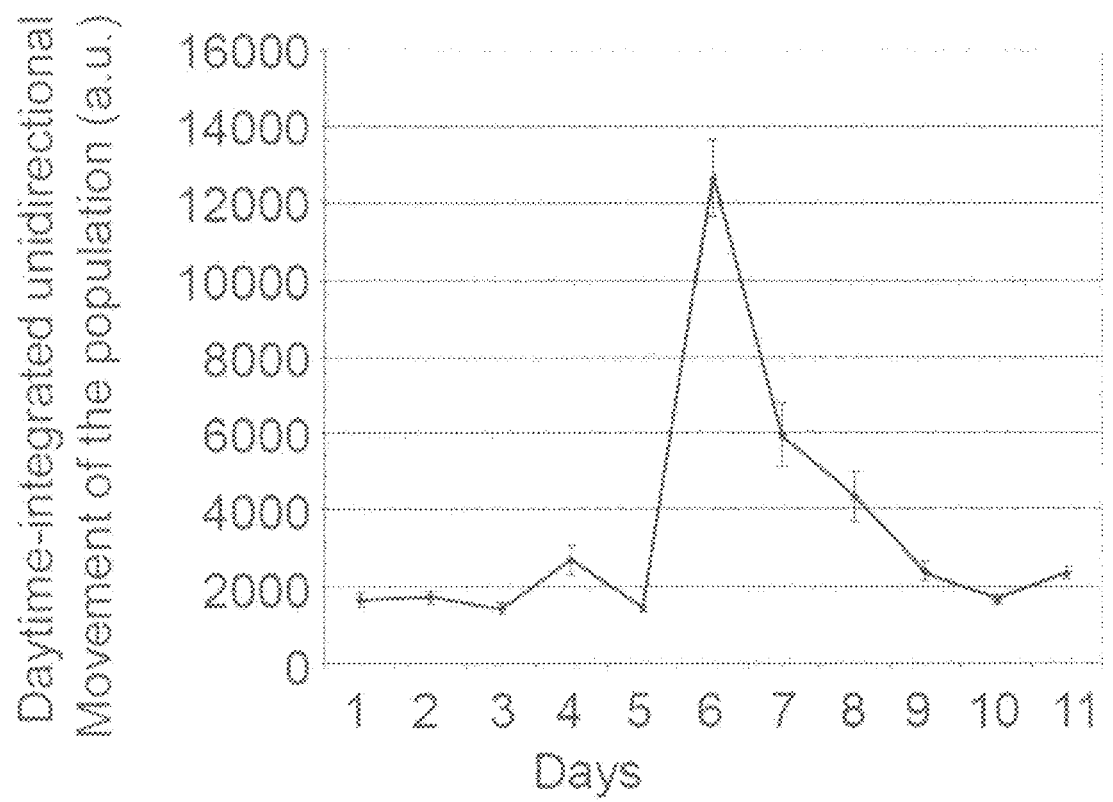
FIGS. 9A-9D show diurnal unidirectional movement of 8 goats around the $19^{th}$ and $20^{th}$ paroxysmal events.
Figure 9B:
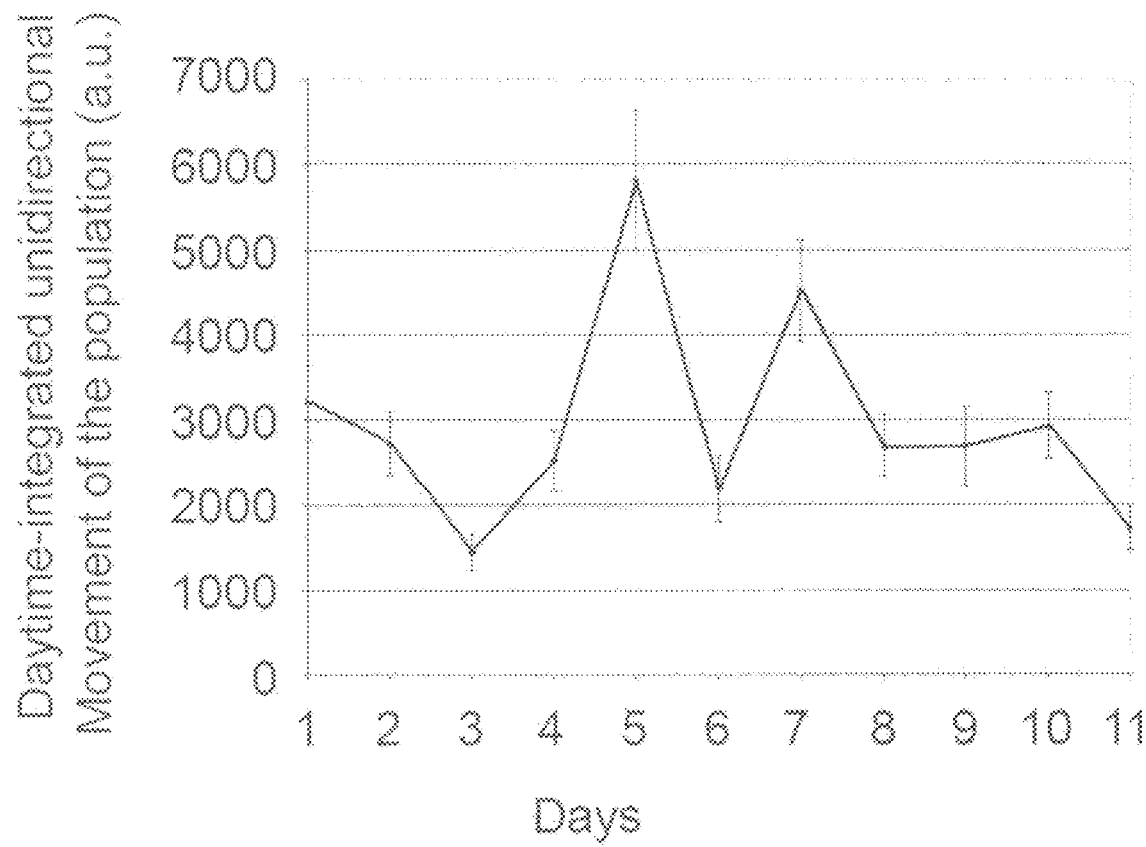
Figure 9C:
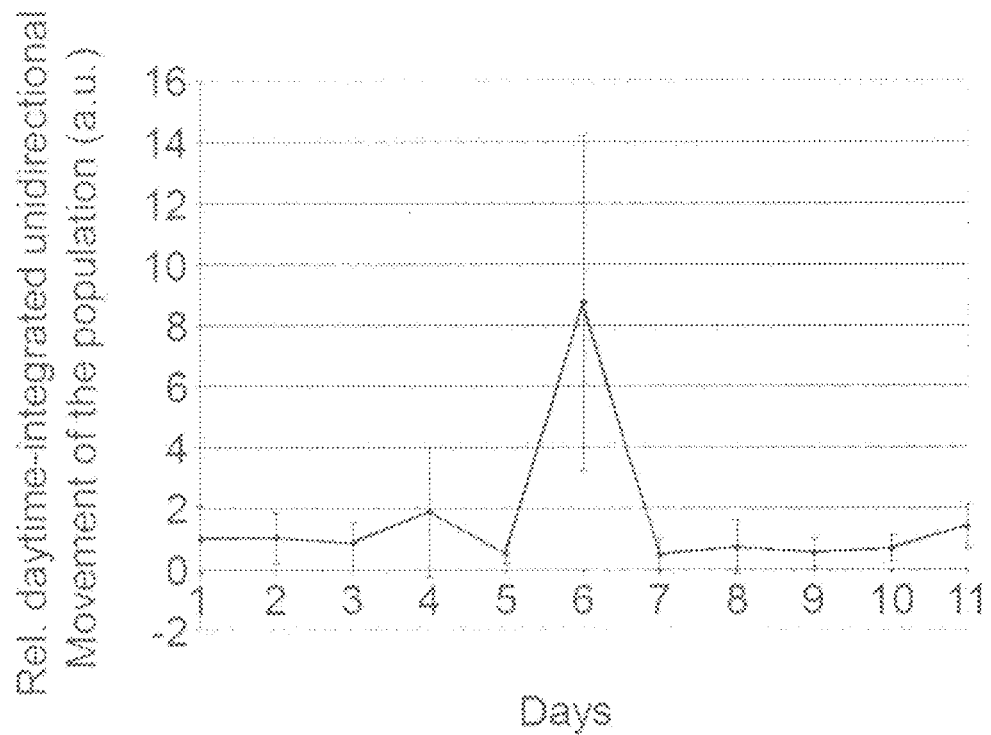
Figure 9D:
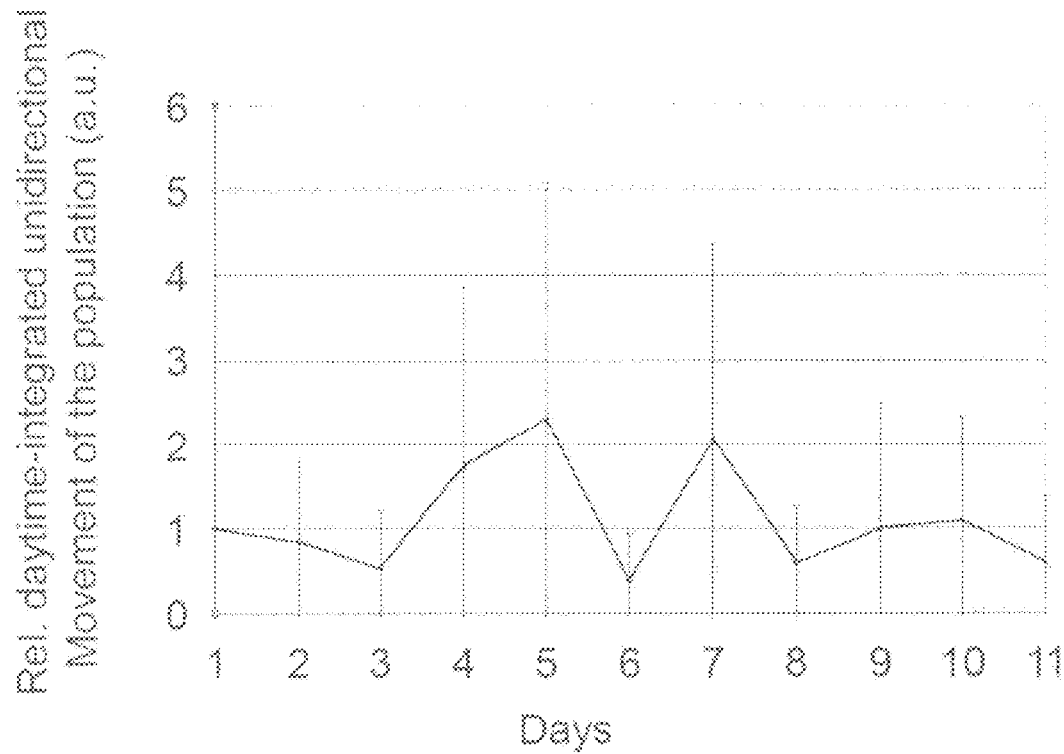

According to another embodiment of the invention, the daytime-integrated unidirectional movement of each animal of the population can be considered in view of the preceding day (cf. FIG. 9C). Consequently the daytime-integrated unidirectional movement of each animal of the population of the first day of the reference profile is normalized to 1. Accordingly, daytime-integrated unidirectional movement of each animal of the population of the following night deviates from the one of the first day by a certain factor. Then the average of all factors of all corresponding animals of the population can be calculated to an overall factor of the population with respect to the preceding day. Repeating this step for every measured day, a reference profile can be generated which gives the relative averaged daytime-integrated unidirectional movement of the population in view of the corresponding preceding day in percent as a function of nights (cf. FIG. 9C).

The alert can be implemented in a single-user warning system, alerting only one recipient or can be part of an alert-network, having several users.

According to an embodiment of the invention, the population of animals can comprise feral and/or semi-domestic and/or domestic animals and/or animals in zoos. Preferably, the population of animals comprises semi-domestic animals. Alternatively, the population of animals can consist of semi-domestic animals. In an example of the invention, the population of animals can comprise land animals and/or aquatic animals and/or aerial animals. Animals which can be used for the forecast can be elephants, ungulates, birds, donkeys monkeys, apes, dolphins, tuna, sea snakes, sea turtles, goats, deer, foxes, badgers, kangaroos, toads, frogs, snakes, seabirds (e.g. boobies and albatrosses), geese, gulls, swallow, insectivorous bats, fruit bats, sheep, cattle, or dogs (feral or domestic). The sea turtles may be used particularly to sense ocean currents and their alterations). Ground-dwelling or cave-dwelling animals can be used in context of the present invention as they may detect environmental changes emanating from the earth's crust first.

Animal species that are highly mobile may not react strongly to local environmental changes, and may thus, not be used for the inventive method and/or system. Animal species that are inadequate in context of the invention can be determined via the lack of their change in behaviour during environmental changes. Initially, some species may give false alarms in certain areas, but threshold decision values will then be adjusted for local conditions.

In the method(s) of the invention the use of higher organisms (vertebrates) is preferred. According to an embodiment of the invention, the population of animals can comprise preferably goats, sheep and/or elephants. For example, elephants may be used to forecast an environmental event, for example to forecast an earthquake. As exemplified herein, in context of the invention goats and/or sheep have successfully been used in the method(s) of the invention. In an example of the invention, the population of animals can comprise animals of the same species. In another example of the invention, the population of animals can comprise animals of different species, such as a mixed population of animals. According to an embodiment of the invention, the population of animals can comprise at least 2, preferably at least 3, at least 4, at least 5, at least 6, at least 7, at least 8, at least 9, at least 10, at least 11, at least 12, at least 13, or more animals. In a preferred aspect of the invention, the population of animals comprises at least 8, at least 12, or at least 13 animals. In an example of the invention, the population of animals lives in a small geographical area, preferably of 200 square-kilometers. A small geographical area may be a single mountain slope. Preferably, the population of animals lives in immediate disaster areas, such as active volcanoes or tsunami-exposed coast lines. The population of animals can be selected according to the best local biological knowledge about the species' reaction during previous environmental changes or catastrophes. It is envisaged that the behaviour and/or physiology of the animals of the population of animals is monitored simultaneously over long periods of time.

In an example of the invention, the at least one acquired behavioural parameter can comprise nocturnal activity and/or 3D-acceleration activity and/or diurnal unidirectional movement. According to an embodiment of the invention, the method for forecasting a type of environmental event can further comprise the steps of: acquiring at least one second data set of at least one behavioural and/or physiological parameter of the population of animals in the presence of the type of environmental event; generating a second reference profile based on said at least one second data set, representing abnormal behaviour and/or physiological status of the population of animals.

In an example of the invention, the presence of an event can be detected using methods comprising visual observation and/or acoustical observation and/or seismological measurement. Given that the type of environmental event is a volcanic eruption, the visual observation may include the description of the altitude of the volcanic eruption and the magnitude of material emitted during an event. The presence of a type of environmental event may also be detected by on-site chemical and geographical/geological measurements. In one particular example of the invention, the magnitude of a type of environmental event can be detected. Accordingly, given that the type of environmental event is a volcanic eruption, minor events in the sense that only small amounts of ashes are emitted or only local lava fountains occur that did not produce lava flowing to the outside of the volcano (Volcanic Explosivity Index (VEI) of 1) may not be detected. Normally, people and animals on the outskirts of the volcano are not visually affected by minor events, and no tremors of earthquakes are felt by humans. In contrast to a minor volcanic event, a major volcanic event (as defined herein below) may be detected by using the inventive method and/or system. With respect to the volcano Etna, examples for major events are the $19^{th}$ paroxysmal event starting as a major event in the evening hours of January 5, 22:20 p.m. (local time), and the $21^{st}$ paroxysmal event starting from March 4, 7:04 a.m. (local time). Official descriptions of these events by the INGV are given in the illustrative examples, below.

In an example of the invention, the threshold value for raising an alert can be determined using the first and second reference profiles. This can be conducted by comparing the first and the second reference profile in the same manner as described with respect to the first reference profile and the test profile, as discussed above. According to an embodiment, the threshold value can be a ratio of 2 or 1.3

According to an embodiment of the invention, the alert is raised at least 20 minutes, at least 30 minutes, at least 40 minutes, at least 50 minutes, at least 1 hour, at least 2 hours, at least 3 hours, at least 4 hours, or at least 5 hours prior to the environmental event. Preferably, the alert is raised at least 1 or at least 2 hours prior to the environmental event. The alert may be raised at least 5 hours prior to the environmental event. Preferably, the alert is raised not longer than 48 hours, 36 hours, 24 hours, or 12 hours prior to the environmental event. Accordingly, using animals to predict natural diseases as described herein allows more time for preparation (such as evacuation) than conventional techniques. In the appended examples a population of goats has been used to forecast environmental events (such as volcanic events) in accordance with the invention and an alert was set at least 5 hours prior to the environmental events. The appended examples also demonstrate that a mixed population of animal species is suitable for the method(s) of the invention. In particular, a mixed population comprising goats and sheep has been used to forecast environmental events (such as volcanic events) and an alert was set at least 2 hours prior to the environmental events.

The invention also provides a system for forecasting a type of environmental event comprising at least one data acquisition unit configured to acquire at least one data set of at least one behavioural and/or physiological parameter of a population of animals; at least one profile generation unit configured to generate at least one first reference profile and/or at least one test profile wherein each profile is based on the at least one data set; at least one ratio calculation unit configured to calculate at least one ratio between the at least one test profile and one of the at least one first reference profile; and at least one alert unit configured to raise an alert if at least one of the at least one calculated ratio reaches a predefined threshold value.

The data acquisition unit can be a bio-logger. This bio-logger may be a biologging tag (E-obs, "Medium GPS-collar"). The data acquisition unit may be a miniaturized bio-logger attached to, or implanted in animals. The data acquisition unit (e.g. the bio-logging tag) can be configured to record the GPS position and/or 3D-acceleration. The data acquisition unit may take sensor samples at various rates: either as requested events or as continuous sampling (e.g., 3D-acceleration at 0.1 Hz to several 100 or 1000 Hz). Preferably, the sampling rate is between 10 to 1778 Hz. The speed of sampling can be adjusted to the behaviour of the specific animal type or individual. The GPS position may be received with the help of a ceramic antenna and GPS position may be calculated on board of the data acquisition unit (such as the biologger) using a GPS chip. Sampling (e.g., of GPS position and/or 3D-acceleration) can be conducted as "timed sampling", e.g., to sample every 2 minutes for 3 seconds. For example, the GPS position may be recorded every 30 minutes and 3D-acceleration may be recorded every 2 minutes.

The profile generation and/or the ratio calculation unit can be integrated in an integrated circuit, a FCPGA (Flip-Chip Pin Grid Array), or a microprocessor. The profile generation unit can also be implemented in a Personal Computer, a mobile device or the like. Also the database Movebank (www.movebank.org) may be used as profile generation unit. The profile generation unit (such as Movebank) may be able to interpret the sensor data transmitted from the animals in almost real time. The data (e.g. the 3D-acceleration data) may be linked to the absolute time of recording which may be determined from a GPS module and GPS location settings. The database Movebank may store the data in a relational data base with the main fields of animal identification number (ID), time, GPS location and movement, GPS error, acceleration, as well as may report on the technical properties of the tag (battery voltage, GPS time to fix, memory status etc). By using the profile generation unit (e.g. Movebank or a PC computer) the data (e.g. acceleration data and/or location data) can be visualized. For example, the acceleration data and the location data may be linked. In one particular example, visualization may be conducted by plotting acceleration values in time and linking it to geographical location as displayed, e.g., on NASA Worldwide or on Google Earth (see FIG. 5). In this particular example, it would be possible to simultaneously watch the behaviour of the animal(s) (e.g., acceleration in the Z-axis) and their locations.

Analyzing an acquired data set (such as acceleration behaviour) in time enables a quantitative determination of the behavioural parameter of (an) animal(s) (e.g. movements of goat(s)) in the Z-axis.

The alert unit can be implemented in an alert system which also uses different conventional alert mechanisms as seismography for example.

According to an embodiment of the invention, the at least one profile generation unit can further be configured to generate at least one second reference profile based on at least one data set, and the at least one ratio calculation unit can further be configured to determine said threshold value based on at least one ratio between one of the at least one second reference profile and one of the at least one first reference profile.

In an example of the invention, the data acquisition unit can comprise a fixing unit which can be configured to attach the data acquisition unit to an animal of the population of animals. According to an embodiment of the invention, the fixing unit can be a neck collar.

In an example of the invention, the data acquisition unit can comprise a sensor unit which can comprise a global positioning system unit configured to generate location coordinates and/or a 3D-acceleration sensor configured to provide roll-pitch-yaw angle data. The 3D-acceleration sensor can be configured to record up and down movements (such as jumping) of an animal of the population of animals. Therefore, the 3D-acceleration sensor may be configured to record the z-axis only. In one particular embodiment of the invention, the data acquisition unit is a 3D-acceleration/GPS collar. It is also envisaged in context of the invention that the data acquisition unit comprises a sensor unit which is configured to sense temperature, humidity, voltage (e.g. EEG, EKG), and/or the production of stress or aggression hormones.

Thus, according to an embodiment of the invention, the sensor unit can comprise means which are configured to measure at least one physiological parameter of the animal comprising an electrocardiograph and/or an electroencephalograph and/or a clinical thermometer and/or means for performing endocrinological measurements (to detect stress hormones, such as corticosterone, testosterone, estradiol) and/or an electromyograph.

The global positioning system unit can be a GPS-(Global Positioning System)-transceiver, a GLONASS-transceiver, a Galileo satellite navigation transceiver, or a BeiDou (Compass) Navigation Satellite System transceiver. It is also envisaged in context of the invention to use a global positioning system unit which is able to determine the location by solar geolocation (e.g. in the oceans) or radio signal triangulation, time of signal arrival.

The 3D-acceleration sensor can be an accelerometer comprising piezoelectric, piezoresistive or capacitive components. Additionally, an anti-aliasing filter can be used. The 3D-acceleration sensor can be used to measure the roll-pitch-yaw angles of an animal of the population of animals. Thus, the 3D-acceleration can be used to determine the activity (i.e. up and down movements, such as jumping) of the animals of the population of animals.

In an example of the invention, the data acquisition unit can comprise a data memory unit and/or a data transmission unit. For example, the memory unit may allow measuring at least one behavioural and/or physiological parameter of a population of animals for several days, such as for at least 14, 20, 50, 100, 180, 200, 500, or 1000 days, preferably 180 days. The memory unit can be a non-volatile memory like a Flash memory, e.g. an USB-Flash drive or a memory chip or a solid state disc. The memory unit can also be integrated in the data base Movebank. For example, Movebank can store the data in a rational data base as described herein above.

The data transmission unit can comprise a transceiver operating in frequency range between from 30 MHz to tens of GHz, preferably between 30 MHz to 10 GHz, more preferably between 30 MHz and 900 MHz. For example, the data may be transmitted via an encrypted 868 MHz data download. During the data transmission, the data acquisition unit may communicate with a base station (e.g. the Basestation b5, e-obs). This base station may be handheld and battery powered. Once data are received by the base station, the base station may erase this part of the memory of the data acquisition unit, allowing the acquisition unit to record new data. The base station may record the data in a memory device, such as a memory chip. Data from the base station may be transmitted (e.g. via a SD memory chip card) to the profile generation unit (such as a computer).

The data transmission unit may allow communication between the data acquisition unit and the user via different means: the data transmission unit can send information at various intervals to a local base receiver station, to a GSM network, a 3G, a LTE, or to a global satellite system. Various schemes of transmission can be implemented (i.e., from real time to several day delay). Intelligent electronic circuits on the data acquisition unit may interpret the observed sensor data on board and transmit data summaries.

According to an embodiment of the invention, the data transmission unit can comprise a transceiver, preferably a VHF transceiver, which is configured to transmit the at least one acquired data set and/or the at least one generated profile and/or the at least one calculated ratio to a remote server unit. In one specific embodiment of the invention, the data acquisition unit comprises a 3D-accelerometer and a GPS-chip and allows real-time VHF-transfer of data to a central data base (Movebank).

The data transmission unit may allow the data acquisition units of different animals to communicate with each other and to transfer information between two or several data acquisition units, either within an individual (e.g. heart rate information transmitted to the backpack data acquisition unit) or between individuals (e.g. proximity to each other or data transfer of the stored data between animals).

In an example of the invention, the data acquisition unit can comprise a power supply. In an example of the invention, the power supply can comprise at least one battery and/or rechargeable battery and/or solar cell. The power supply may be a battery, a long-lasting power supply (>1 year) and/or may be recharged by biogenic or external power sources such as solar power.

According to an embodiment of the invention, the system for forecasting a type of environmental event can further comprise a remote server unit wherein the remote server unit can comprise the data memory unit and/or the profile generation unit and/or the ratio calculation unit and/or the alert unit. In an example of the invention, the profile generation unit can comprise a processing unit and/or a filter unit and/or or a pattern recognition algorithm. The filter unit can comprise a FFT filter or a percentile filter or a computer machine learning algorithm or the like.

In one aspect of the invention, a satellite-based small-object tracking system, e.g. the ICARUS system, may be used to in context of the herein described method and/or system. Exemplarily, the system and the method described herein can be controlled and monitored using said satellite-based small-object tracking system. The inventive method and/or system can be used at any spatial (square meters to continents) and temporal (days to years and decades) scale, with any group of animals (wild or captive).

The invention also relates to a computer program product comprising one or more computer readable media having computer executable instructions for performing the steps of the method for forecasting a type of environmental event.

An advantage of the inventive method and system over the state of the art is that it can be used in areas where no elaborate measurement network (such as sophisticated local seismic equipment) exists (e.g., remote areas of the globe such as parts of the seismically highly active Philippines) or where such methods have not been developed (e.g. certain Tsunami areas).

To anticipate disaster is worth billions of dollars annually. Examples are technical tornado warning systems or tsunami warning systems. Accordingly, another advantage of the inventive method and/or system is to provide a low-cost immediate alert system.

The term "forecasting" as used herein means making statements about events whose actual outcomes (typically) have not yet been observed. More specifically, "forecasting of a type of environmental event" means to recognize that a type of environmental event (such as a major volcanic event or a tsunami) is imminent. A type of environmental event may be forecasted at different time points, for example hours to days before the type of environmental event occurs. For example, 5 hours before a type of environmental event (such as a major volcanic event) is happening, it may be recognized that said environmental event will occur.

The term "data set" as used herein relates to data (e.g. values) derived from a consecutive row of single measurements. In context of the invention, the data set may comprise values corresponding to the measurement of behavioural and/or physiological parameters (as defined herein above and below). The data set can comprise a plurality of data points acquired in an instant or in a predefined time interval. For example, the position of each animal of the population of animals, representing the movement of the animal, can be acquired every 30 minutes for 10 days, leaving to a sub-data set of 480 points for each animal. The sub-data sets of each animal of the population can be combined to a joint data set.

The term "type of environmental event" as used herein relates to a natural disaster which is the effect of earths natural hazards, for example flood, tornado, hurricane, volcanic eruption, earthquake, heat wave, or landslide. Types of environmental events include geological disasters, such as avalanches, earthquakes, and volcanic eruptions (specifically major volcanic events as defined herein, above and below). Other types of environmental events are hydrological disasters, like floods, limnic eruptions, and tsunamis. Also meteorological disasters, such as blizzards, cyclonic storms, droughts, and hailstorms are included by the term "type of environmental event". In a preferred aspect of the invention, the type of environmental event is an earthquake, a marine earthquake, a tsunami, and a volcanic event. More preferably, the type of environmental event is a volcanic event, and most preferably, a major volcanic event. A major volcanic event/activity means that large amounts of ash are emitted and that the lava fountains produce lava flows at the outside of the volcano. A major volcanic event has a Volcanic Explosively Index (VEI) of 2. In general, people and animals on the outskirts of the volcano are visually affected by major volcanic events, and tremors of earthquakes are felt by humans. The type of environmental event that is forecasted with the inventive method and/or system may also by damaging volcanic event, which has a VEI of 3.

The term "behavioural parameter", in particular in the context of "acquiring [ . . . ] [a] data set of [a] behavioural parameter" means to analyze a specific aspect of the behaviour of animals in a population of animals. For example, a "behaviour parameter" as used herein may be the activity of the animals. The activity may be analyzed by measuring the 3D-acceleration. By using a 3D-accelerometer, up and down movements (such as jumping) of animals may be detected. Another "behavioural parameter" can be the movement of an animal, such as the unidirectional movement during a particular period of time. To quantitatively analyze and compare the linear movements (i.e. unidirectional movement) of animals (such as goats) during the day, the total daily distance travelled by the animals from their nocturnal resting location to their evening resting location in a linear way may be used to represent the unidirectional movements of animals during a day. The diurnal unidirectional movement of animals can be determined by the GPS position of the animals. The term "physiological parameter", in particular in the context of "acquiring [ . . . ] [a] data set of [a] physiological parameter" means to analyze a specific aspect of the physiological status of animals in a population of animals. For example, a "physiological parameter" may be the heartbeat, the brain activity, the muscle electrical activity, the temperature, and/or the presence and/or amount of stress hormones (such as corticosterone, testosterone, or estradiol). These "physiological parameters" may be measured by using an electrocardiograph, an electroencephalograph, an electromyograph, or a clinical thermometer, or by performing (an) endocrinological measurement(s).

The term "reference profile" as used herein means a profile that is used as a reference. In context of the present invention, the "first reference profile" is based on a data set that has been acquired in the absence of a type of environmental event and thus, represents "normal" behavioural and/or physiological status of animals in a population of animals. The "second reference profile" as used herein is based on a data set that has been acquired in the presence of a type of environmental event and thus, represents "abnormal" behavioural and/or physiological status of animals in a population of animals. Accordingly, in context of the present invention, the first and second reference profile may be used (e.g. compared) to determine the threshold value which is used to recognize a type of environmental event. The "test profile" as used herein is based on a data set that is acquired to forecast a type of environmental event.

The term "population of animals" as used herein relates to a group of organisms that live in the same geographical area. The animals of the population of animals may belong to the same species. The population of animals may comprise at least 2, preferably at least 3, at least 4, at least 5, at least 6, at least 7, at least 8, at least 9, at least 10, at least 11, at least 12, or more animals. In a preferred aspect of the invention, the population of animals comprises at least 8 or at least 12 animals. The population of animals may be a population of semi-domestic animals. The population of animals can be a population of goats (such as semi-domestic goats). As described herein, the population of animals can live in a small geographical area (i.e. within a weekly home range of an animal), preferably the area is about 200 square-kilometres. Preferably, the population of animals lives in immediate disaster arrears, such as active volcanoes or tsunami-exposed coast lines.

The term "ratio" as used herein relates to a comparison of profiles. In a particular example of the invention, the term "ratio" relates to the comparison of a test profile and one (or several) reference profile(s). This also includes the comparison of an instant value of a test profile with the average of the values of one (or several) reference profile(s). The term "ratio" also means the comparison of a test profile (or one instant value of a test profile) with the average of several reference profiles or with the average of the values of one or several reference profile(s). The comparison can be performed by any visual or mathematical means. For example, one may analyse the manifold increase of a test profile (or an instant value of a test profile) in comparison to one or several reference profile(s). For instance, in comparison to the average of the values of a reference profile, a test profile (or one instant value of a test profile) may be 2-fold or 1.3-fold increased. In another example, one may analyse the percentage increase of a test profile (or an instant value of a test profile) in comparison to one or several reference profile(s). For instance, in comparison to the average of the values of a reference profile, a test profile (or one instant value of a test profile) may be increased for 100% or for 30%.

In context of the present invention, the proof of principle of the inventive method and system for forecasting a type of environmental event by using a population of animals has been demonstrated by the appended examples and the supplementary notes herein above.

The present invention is further described by reference to the following non-limiting figures and examples.

The Figures show:

FIG. 1. Schematic overview of magma within Mt. Etna, Sicily; Picture from Prof. Ulrich Schreiber, personal communication.

Figure 2:
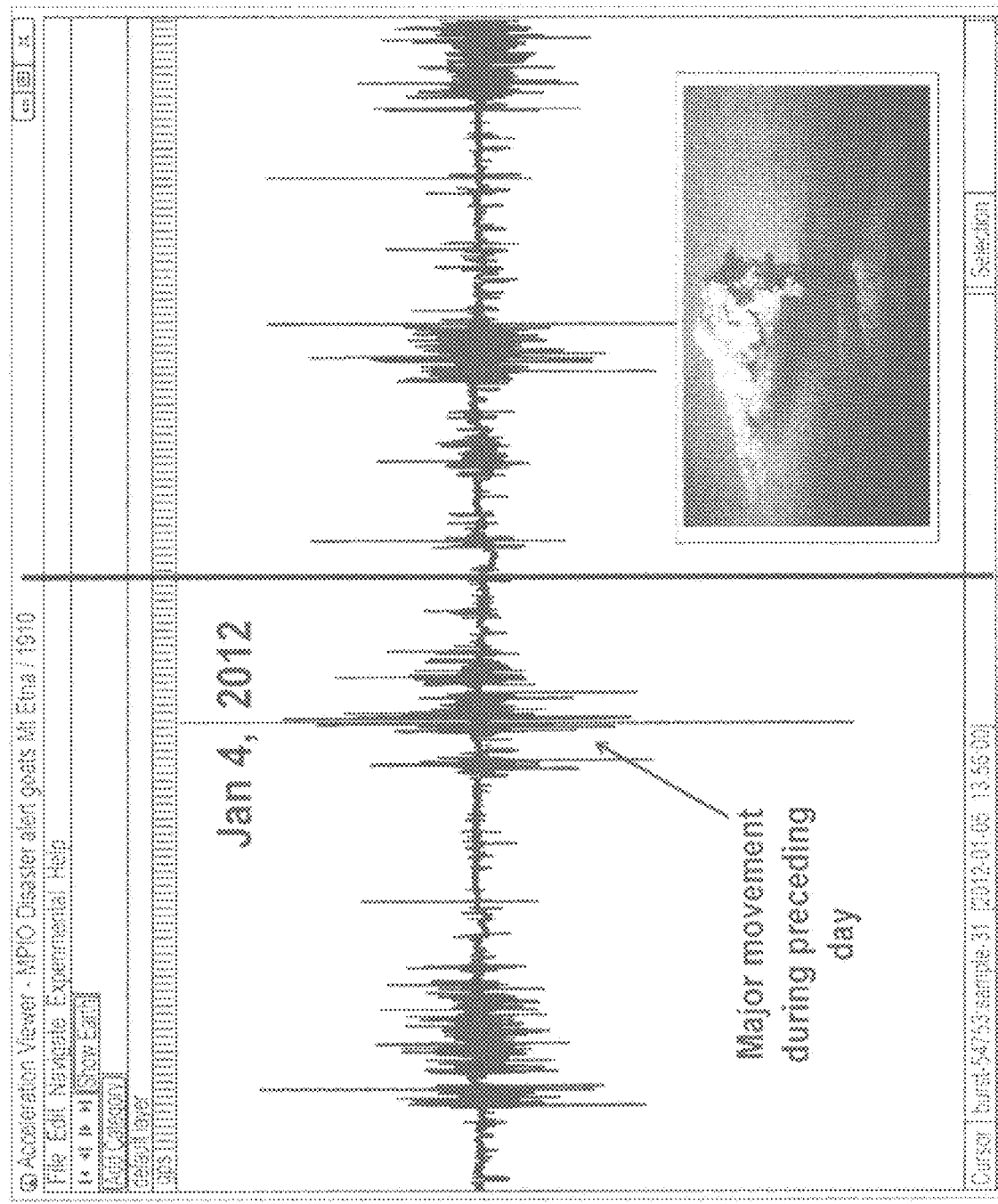
FIG. 2 is a screenshot from Movebank's acceleration viewer, indicating an occurrence of a major volcanic event of Jan. 4, 2012.

FIG. 2. Screenshot from Movebank's acceleration viewer. The acceleration of one goat for 4 days and nights around a major volcanic event is shown. The X-axis shows time in days, minutes, seconds (depending on magnification), the y-axis shows the arbitrary acceleration units in relation to the overall average acceleration for an individual goat. The occurrence of the major volcanic event of January 4, 22:20 h local time, is indicated by a vertical line. Major unidirectional movement of the goat during the preceding day is indicated by an arrow.

The photograph shows an eruption column and lava fountain from the New Southeast Crater seen from an airplane passing to the northeast of Etna during the Jan. 5, 2012 eruptive episode (photo taken by Gloria Guglielmo; original photo on Flickr).

Figure 3:
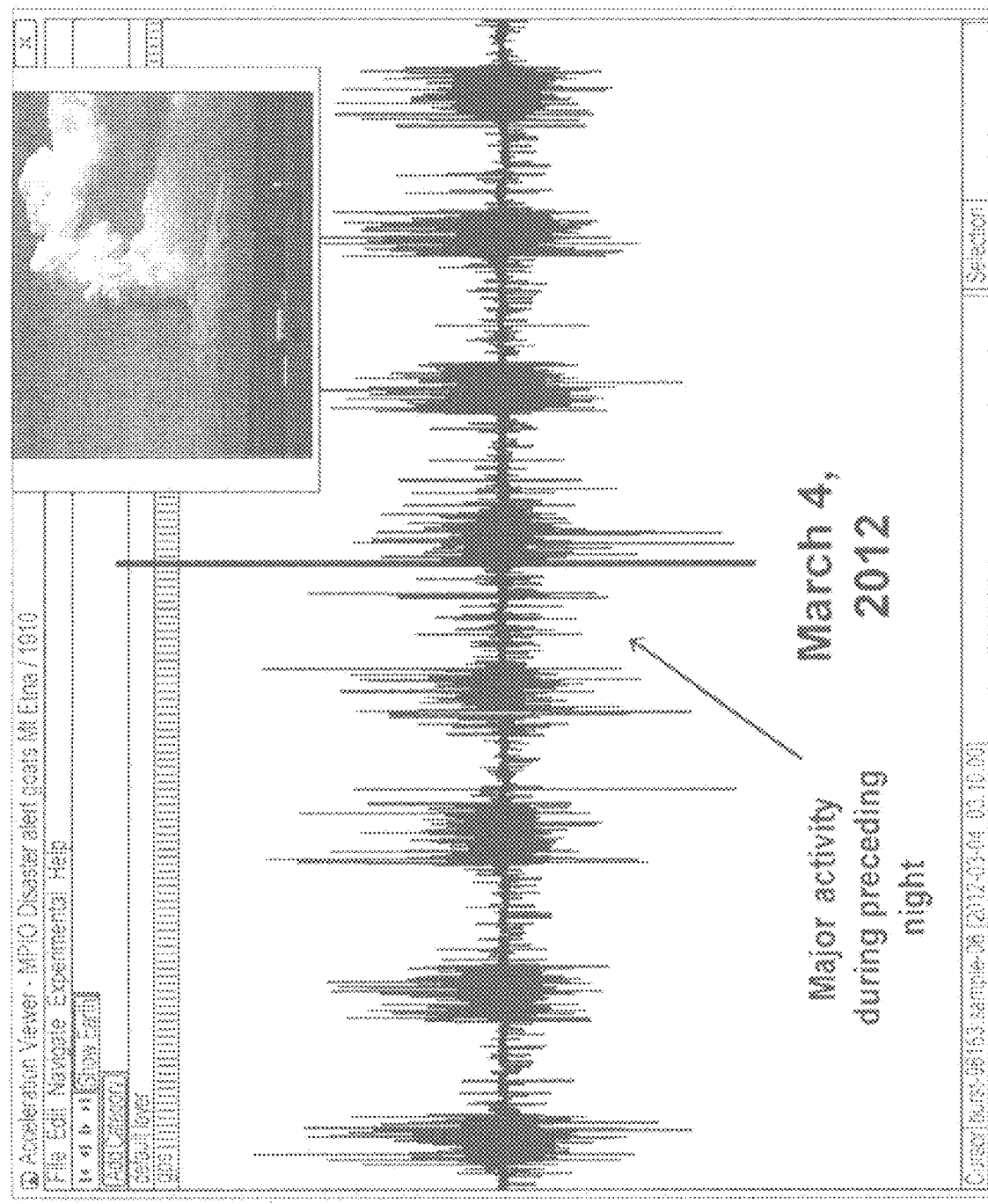
FIG. 3 is a screenshot from Movebank's acceleration viewer, indicating an occurrence of a major volcanic event of Mar. 4, 2012.

FIG. 3. Screenshot from Movebank's acceleration viewer. The acceleration of one goat for 8 days and nights around a major volcanic event is shown. The X-axis shows time in days, minutes, seconds (depending on magnification), the y-axis shows the arbitrary acceleration units in relation to the overall average acceleration for an individual goat. The occurrence of the major volcanic event of Mar. 4, 2012, 7:04 h local time, is indicated by a vertical line. Major activity of the goat during the preceding night is indicated by an arrow.

The photograph shows an eruption column of the Mar. 4, 2012 paroxysmal eruptive episode seen from the Catania plain, about 40 km southwest of the summit of the volcano (photographed by da Elisabetta Ferrera; University of Catania).

Figure 4:
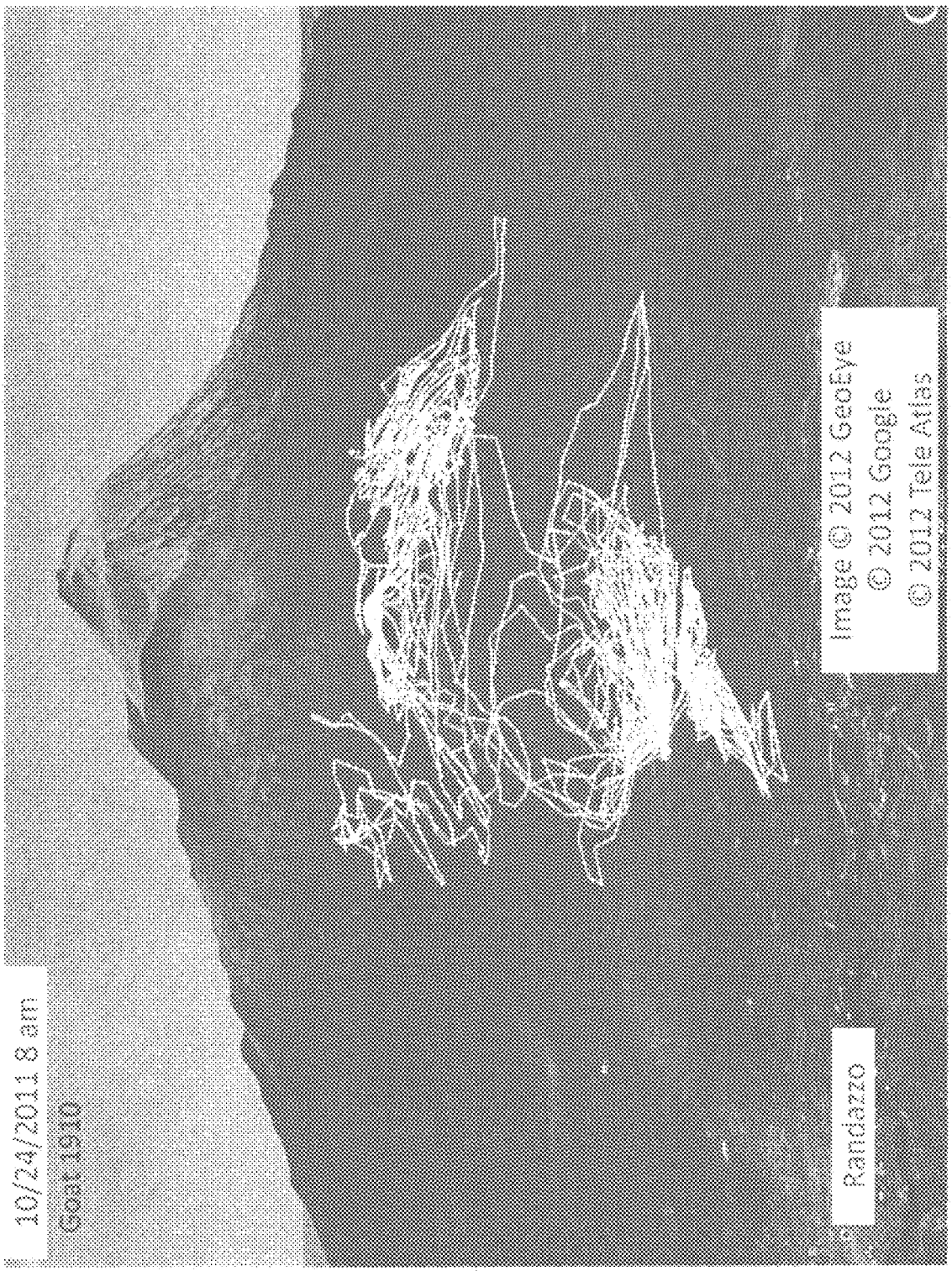
FIG. 4 is a screenshot from Movebank's acceleration viewer demonstrating movements of one goat around Mt Etna.

FIG. 4. Movements of one goat. The screenshot from Movebank's acceleration viewer demonstrating the movements of one goat around Mt Etna is shown. The location of the goat was measured by GPS.

Figure 5:
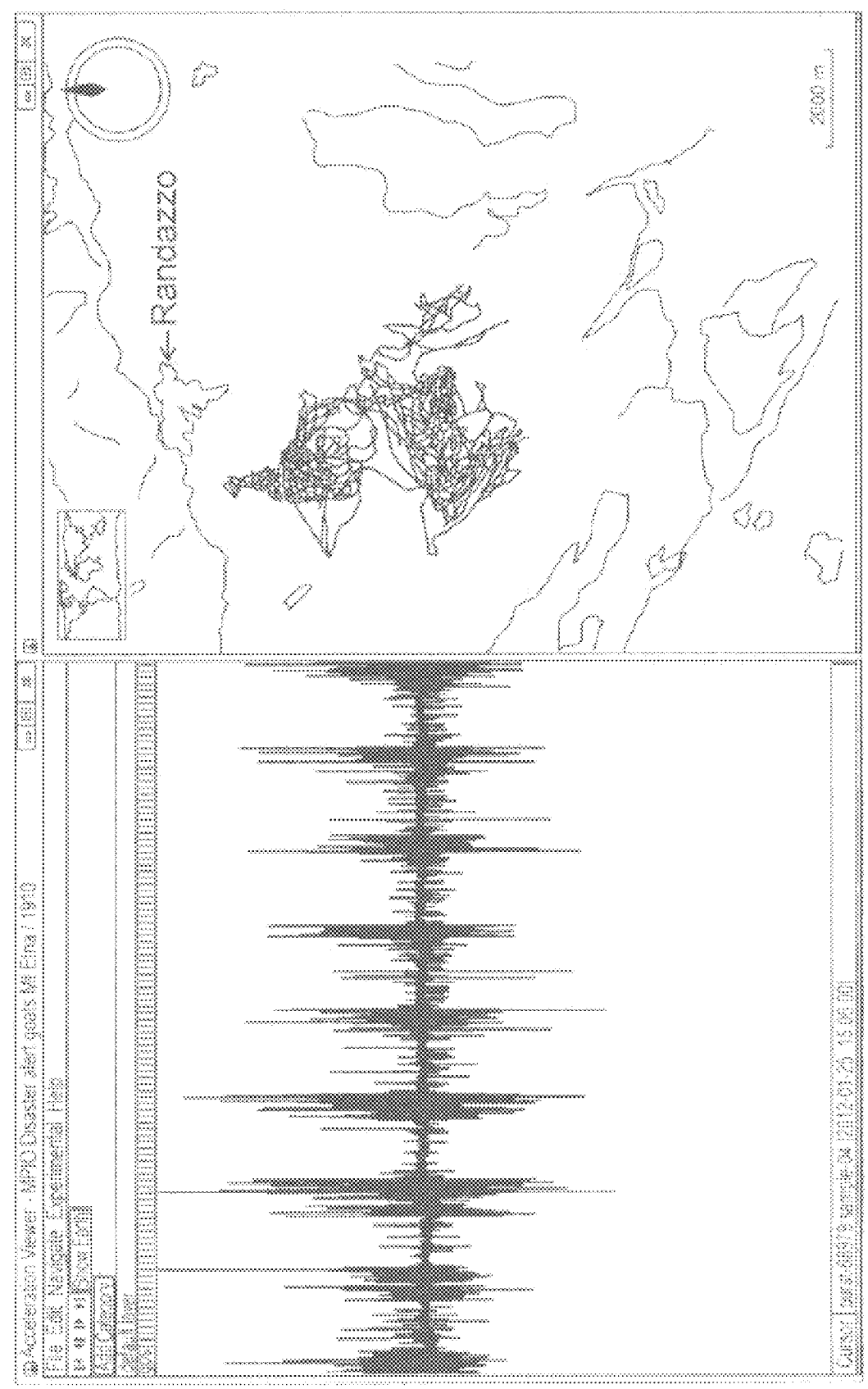
FIG. 5 is a screenshot from Movebank's acceleration viewer demonstrating acceleration and location of one goat.

FIG. 5. Linking of acceleration data to location data of one goat. The screenshot from Movebank's acceleration viewer demonstrating acceleration and location of one goat is shown. The left panel shows the acceleration of the goat #1910 for 9 days and nights. The X-axis shows time in days, minutes, seconds (depending on magnification), the y-axis shows the arbitrary acceleration units in relation to the overall average acceleration for an individual goat. The right panel shows the movements of the goat around Mt Etna during this period (lower right in the Worldwind picture).

Figure 6:
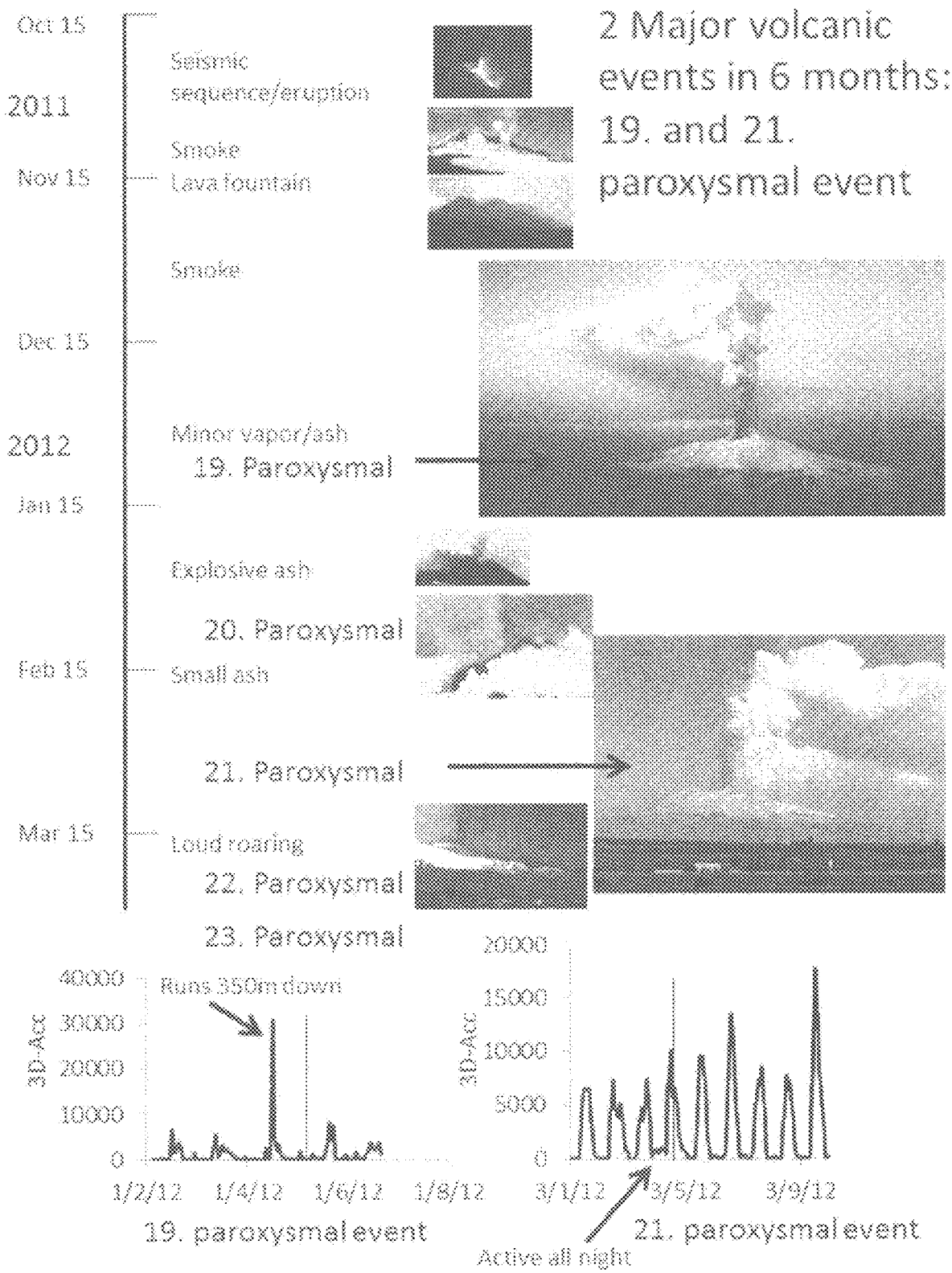
FIG. 6 is a diagram showing diurnal unidirectional movement and nocturnal activity of one goat around $19^{th}$ and $21^{st}$ paroxysmal events.

FIG. 6. Diurnal unidirectional movement and Nocturnal activity of one goat around the $19^{th}$ and $21^{st}$ paroxysmal events. A time scale including the major and minor volcanic events is shown on the left. Some of the volcanic events also shown on photographs (photos from INGV). The large photograph indicated by the arrow as "19. Paroxysmal" shows an eruption column and lava fountain from the New Southeast Crater seen from an airplane passing to the northeast of Etna during the Jan. 5, 2012 eruptive episode (photo taken by Gloria Guglielmo; original photo on Flickr). The large photograph indicated by the arrow as "21. Paroxysmal" shows an eruption column of the Mar. 4, 2012 paroxysmal eruptive episode seen from the Catania plain, about 40 km southwest of the summit of the volcano (photographed by da Elisabetta Ferrera; University of Catania).

The graphs show 3D-acceleration of one goat around the $19^{th}$ (left graph) and the $21^{st}$ (right graph) paroxysmal events. The occurrence of the major volcanic event is indicated by vertical lines. The graph on the left shows that on the day before the major volcanic event, the goat showed enhanced diurnal unidirectional movement (i.e. it runs 350 m down). The graph on the right shows that the night preceding the major volcanic event, the goat showed enhanced activity (i.e. it was active all night).

FIG. 7. Nocturnal activity of 8 goats around the $21^{st}$ and $22^{nd}$ paroxysmal events. The major event starts at 7:04 a.m. (local time) after the $6^{th}$ night. A and B: The graphs are showing the overnight-integrated activity of the population of 8 goats around a major volcanic event ($21^{st}$ paroxysmal event; A) and a minor volcanic event ($22^{nd}$ paroxysmal event; B) including the standard deviation as error bars in arbitrary units (a.u.).

C and D: The graphs are showing the relative overnight-integrated activity of the population of 8 goats around a major volcanic event ($21^{st}$ paroxysmal event; C) and a minor volcanic event ($22^{nd}$ paroxysmal event; D) including the standard deviation as error bars.

The graphs demonstrate that in the night before the major volcanic event, the population of animals shows an increase of nocturnal activity of at least 100% as compared to the activity of the five preceding nights. In contrast, the population of animals does not show such an increase in nocturnal activity in a night before a minor volcanic event.

Figure 8:
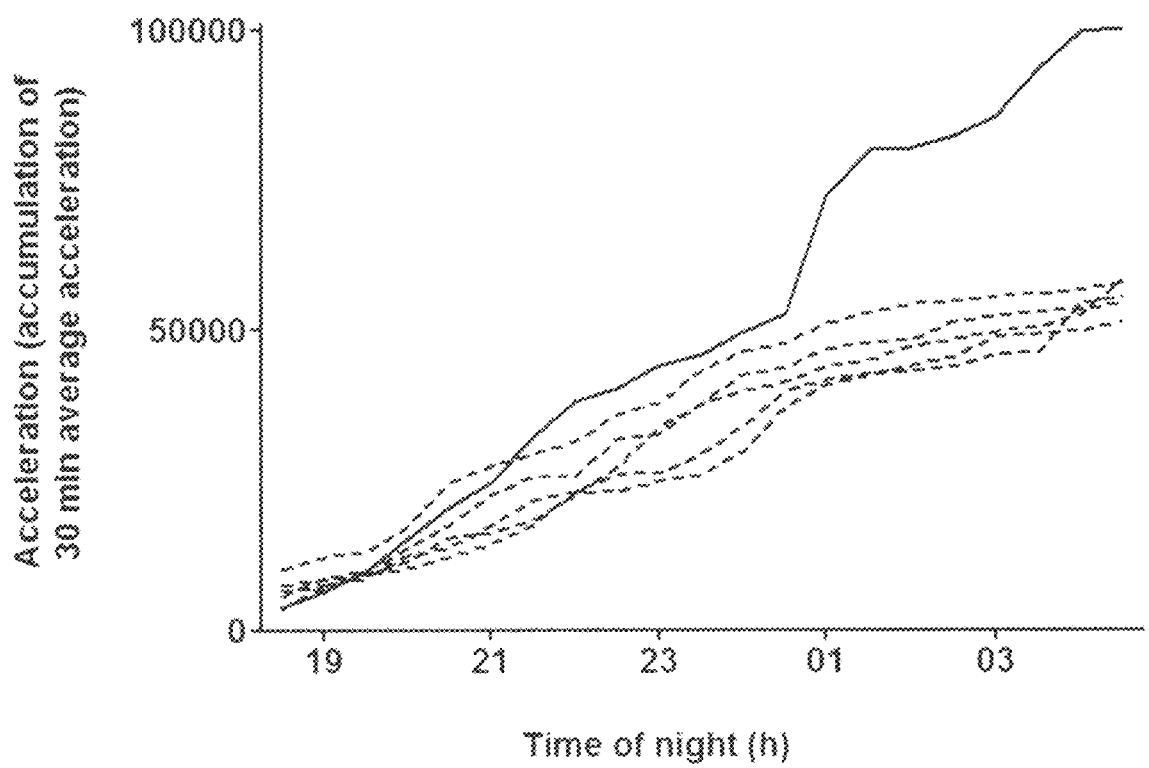
FIG. 8 shows accumulation of average activity of 8 goats during the night preceding a volcanic event.

FIG. 8. Accumulation of ½-hourly activity of 8 goats during the night preceding a volcanic event. In 6 nights preceding different volcanic events, the average 3D-acceleration activity of 8 goats has been determined every 30 min and each measured value has been summated to the foregoing values, so that the graphs show an accumulation of the measured activity values. The accumulation curves of average acceleration behaviour of 8 goats for 5 control nights preceding a minor volcanic event, compared to the night preceding the major volcanic event (line which is above all other lines starting from 21:30) is shown. Please note the jump in acceleration of this line of at least 30% after 1:00 hours of the night preceding a major volcanic event. The major volcanic event occurred ca. 5 hours later. In the 5 nights preceding a minor volcanic event, no jump in acceleration of at least 30% occurs.

FIG. 9. Diurnal unidirectional movement of 8 goats around the $19^{th}$ and $20^{th}$ paroxysmal events. The major event starts at 22:20 p.m. (local time) after the $6^{th}$ day. A and B: The graphs are showing the daytime-integrated unidirectional movement of the population of 8 goats around a major volcanic event ($21^{st}$ paroxysmal event; A) and a minor volcanic event ($22^{nd}$ paroxysmal event; B) including the standard deviation as error bars.

C and D: The graphs are showing the relative daytime-integrated movement of the population of 8 goats around a major volcanic event ($21^{st}$ paroxysmal event; C) and a minor volcanic event ($22^{nd}$ paroxysmal event; D) including the standard deviation as error bars.

The graphs demonstrate that the day before the major volcanic event, the population of animals shows an increase of unidirectional movement of at least 100% as compared to the unidirectional movement of the five preceding days. In contrast, the population of animals does not show such an increase in unidirectional movement the day before a minor volcanic event.

Figure 10:
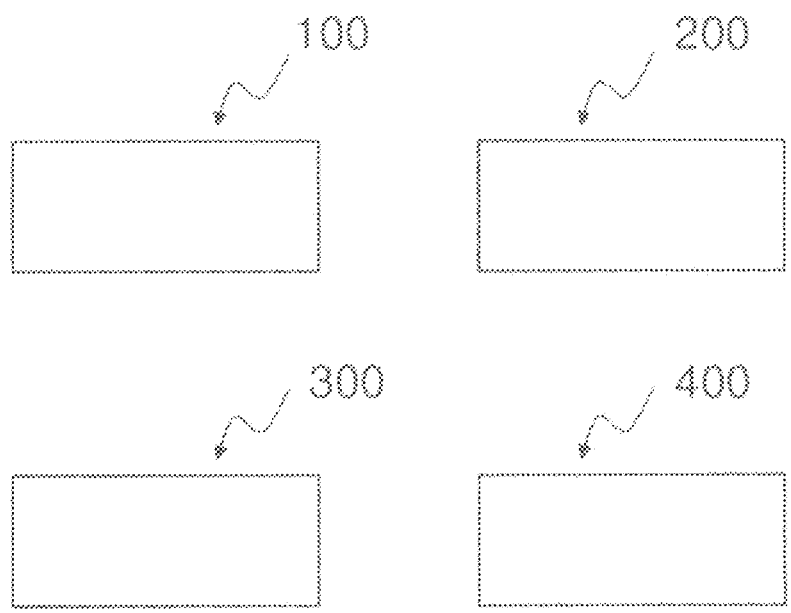
FIG. 10 is a diagram illustrating components of a system according to an example embodiment.

FIG. 10. Overview of the system of the invention according to one embodiment of the invention. The system comprises a data acquisition unit (100), a profile generation unit (200), a ratio calculation unit (300), and an alert unit (400).

FIG. 11. Overview of the data acquisition unit (100) and the sensor unit (120) according to one embodiment of the invention. The data acquisition unit (100) comprises a fixing unit (110), a sensor unit (120), a data memory unit (130), a data transmission unit (140), and a power supply (150). The sensor unit (120) comprises a global positioning system receiver (121), a 3D-acceleration sensor (122), and means configured to measure at least one physiological parameter (123).

Figure 12:
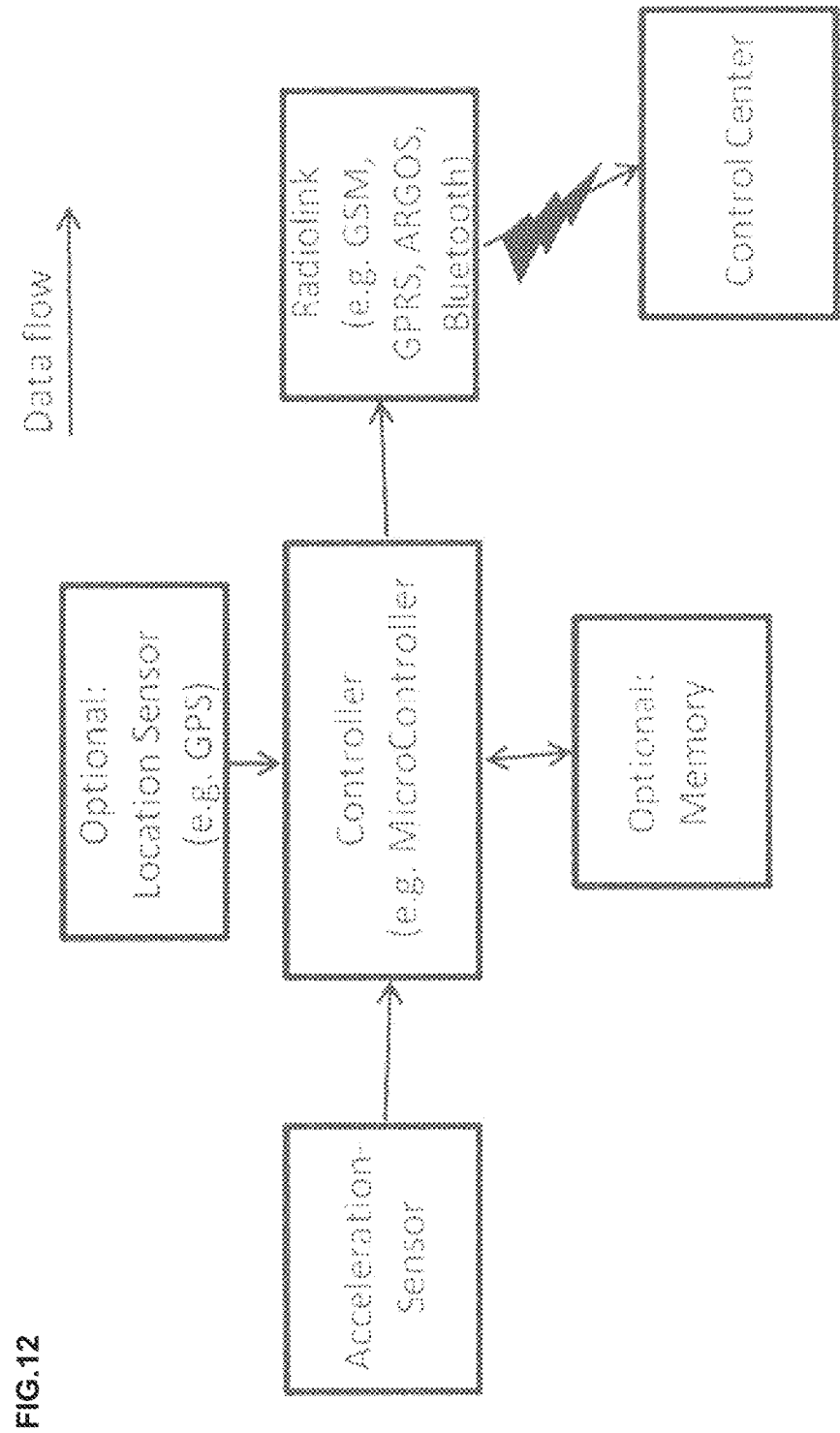
FIG. 12 illustrates a configuration of a data acquisition unit according to one embodiment of the invention.

FIG. 12. Overview of the data acquisition unit (100) according to one embodiment of the invention. The data acquisition unit (100) is a biologger (e-obs) comprising an acceleration sensor, optionally a location sensor (e.g. GPS), a controller (e.g. MicroController), a radiolink (e.g. GSM, GPRS, ARGOS, Bluetooth), and a control center.

Figure 13:
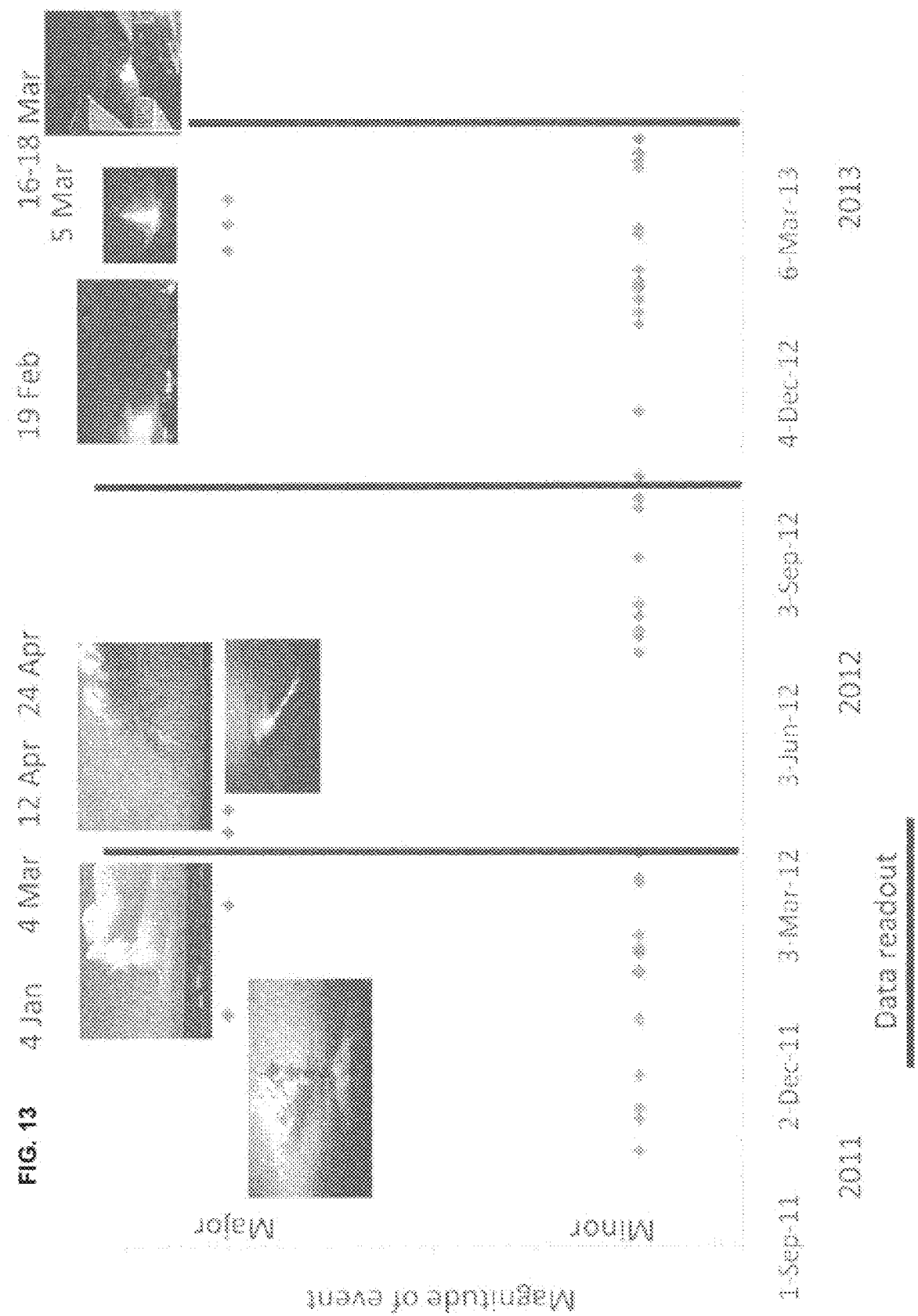
FIG. 13 illustrates a time line of volcanic events at Mt. Etna during a study period.

FIG. 13. Time line of volcanic events at Mt. Etna during a study period. Each dot represents a significant volcanic event starting on Sep. 1, 2011 until 25 Apr. 2013. The dates of major events are indicated and small insect pictures depict the magnitude of the event. Vertical lines indicate data readout periods. In Example 2, two major events have been detected. In Example 3 five additional major events have been detected, totalling seven major events.

Figure 14:
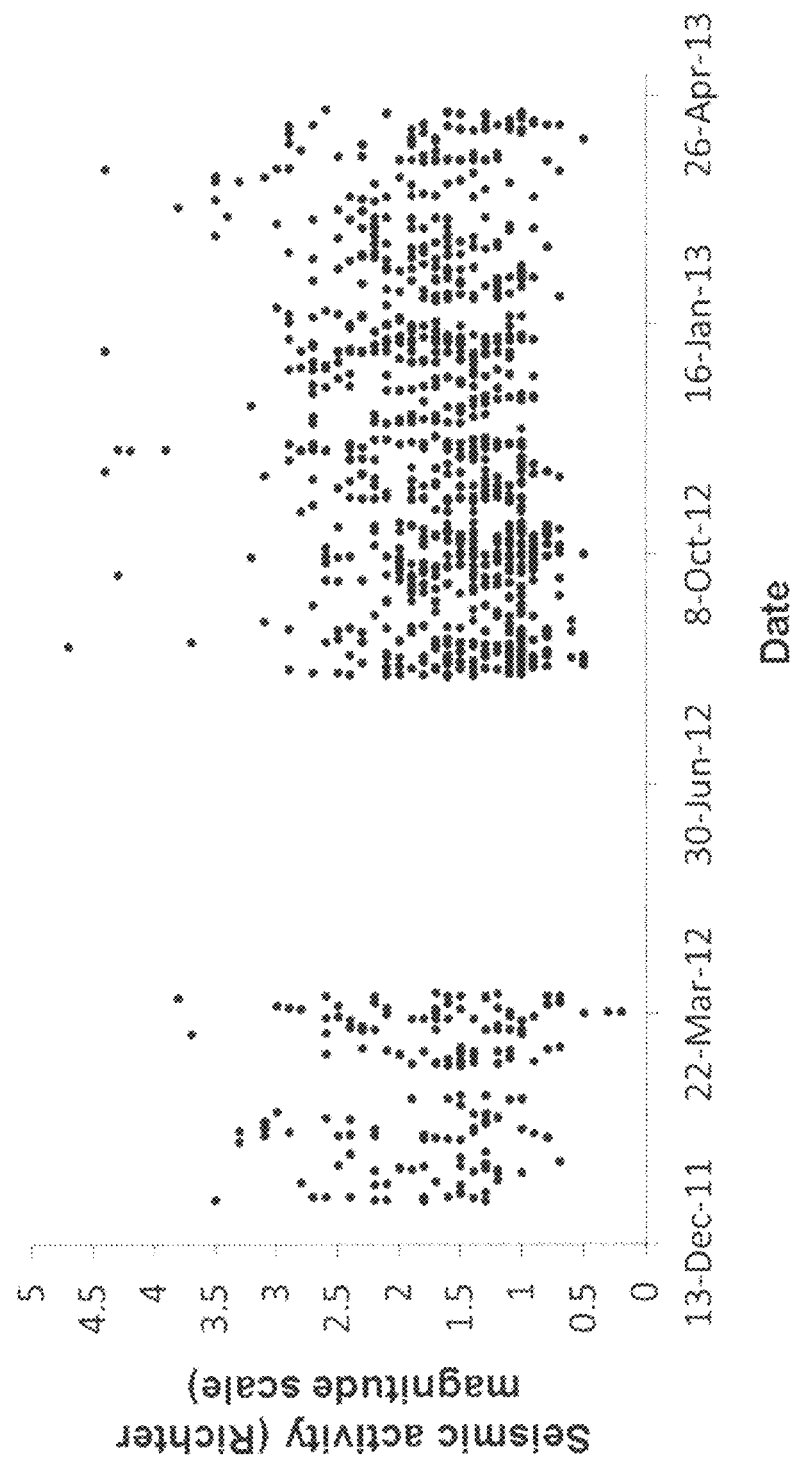
FIG. 14 shows low seismic activity (e.g., below 5 on the Richter magnitude scale) at Mount Etna that does not coincide with volcanic event.

FIG. 14. Low seismic activity (i.e. below 5 on the Richter magnitude scale) at Mount Etna does not coincide with volcanic event. Each dot indicates an earthquake and its magnitude. No data are available for the period from April to September 2012.

The Examples illustrate the invention.

EXAMPLE 1

Materials and Methods
Study Site

Fieldwork was carried out from April 2011 to October 2011 on the Mediterranean island of Sicily to determine whether feral goats show behaviors that could be used to anticipate and predict natural disasters. The study was conducted on the northern slopes of Mount Etna volcano, around the small town of Randazzo (37.8752 W, 14.9524 N). The study site consists of feral pastures on the outskirts of the town, as well as natural forests and openings in the vegetation along the slopes of the volcano at an altitude of ca. 1000 to 1900 meters above sea level. This altitude was chosen because Mt. Etna hosts magma chambers that horizontally extend from a central magma chimney towards the slopes of the volcano (see FIG. 1). It is expected that gases from the magma chambers may escape at these altitudes and potentially be detectable by organisms.

Study Objects: Semi-Domestic Goats

We used adult female semi-domestic goats as study subjects because initial interviews with local naturalists and goat herders indicated that goats are the most sensitive animals towards natural changes in the area. The goats used in this experiment were chosen randomly from a captive herd of ca. 500 goats, all belonging to one farmer. All of these goats are locally adapted to the prevailing environmental conditions and herded in the area since presumably hundreds of years. These goats roam freely around the slopes of Mt. Etna for most of the year, but are brought down from the mountain during the time of calving (March/April) and harvesting (October) each year. The goats form small herds, usually three to a dozen goats, in a fission-fusion manner. Thus, the goats observed here were usually roaming around without immediate contact to other observed goats. However, at rare random times, collared goats were moving in the same herd and thus could not be considered independent units for statistical analysis. During the two times when Mt. Etna erupted in a substantial way (see below) within the observation period, all observed goats were roaming independent of each other, thus we considered all 8 individuals as independent.

Biologging Tags and Attachment

We used biologging tags from E-obs (www.e-obs.de) to determine the behavior and location of goats for up to 180 days (until the tag memory fills up). The tags were attached as neck collars to the goats in a simple procedure, i.e., one goat herder was holding the goat by the horns while standing above the goat with the legs pressing against the body of the boat, the other herder was putting the collar around the neck and tightening the self-tightening screws of the collar such that a two-finger opening remained between the collar and the goats' neck. In this way we ensured that the goats was minimally disturbed by the collars, similar to bell collars put on regularly by the goat herders to approximately every $20^{th}$ goat in a heard.

Measurements Taken by the Tags

The e-obs tags recorded GPS position every 30 minutes as well as 3-D acceleration every 2 minutes for 3.6 seconds. The GPS signal was received with the help of a ceramic antenna and GPS position was calculated on board of the biologger using a commercial GPS chip. GPS timeout was set to 2 minutes, i.e., if the GPS receiver chip could not calculate a GPS position within 2 minutes, it would give up and try again 28 minutes later to get a GPS fix. This happened rarely whenever the goats were inside a concrete farmhouse with a metal roof. At all other times, the average time to a GPS fix was 28 seconds, ranging from 3 to 92 seconds.

Acceleration was recorded in the z-axis only, to report the up and down movements of the goats, which we deemed sufficient to allow for an understanding of goat behavior. Only recording every 2 minutes for a short interval, and only recording the Z-axis of the accelerometer, massively reduces the amount of data that needs to be stored, transmitted and analyzed. The observation scheme represents the 'timed sampling' method that is well established in behavioral analysis and is known to report the behavior of individuals with high accuracy (Altman 1965).

The accelerometer used in the e-obs tags is a 3D-accelerometer. In general accelerometers have some kind of a piece of mass that is connected to a flexible material and a damping material. The mass is pushed against the flexible material by the acceleration, and the excitation is proportional to the acceleration. The damping material prevents oscillation. As a consequence the output is (for low frequencies) proportional to the acceleration. For higher frequencies the sensor becomes less sensitive (this is true for all types of sensors) and there will be some phase shift (this is also true for all types of sensors). The bandwidth used in e-obs tags is 150 Hz for the Z-axis and typically 350 Hz for the X- and Y-axis. The analog output signal is sampled with a user-adjustable sampling rate ranging from 10 Hz to 1778 Hz for all axes combined. Here we used 10 Hz.

There is no anti-aliasing filter, which means that the user must be sure that acceleration doesn't oscillate with a frequency higher than half the sampling frequency. For example: If the sampling frequency is 10 Hz for one axis, then e.g. the jumping frequency of a goat should not be more than 5 Hz, otherwise the user will get the wrong jumping frequency during analysis. All XYZ axes are perpendicular to each other like a cartesian coordinate system. Acceleration can never be used to predict positions, because you have to mathematically integrate twice to retrieve position from acceleration. This, however, implies that you also integrate the errors. Additionally the axes are fixed relative to the goat, but the animal's orientation is not fixed relative to space, so you never know the direction of acceleration relative to space/earth. The data values are 12 bit-readings of the analog-to-digital converter and are not calibrated. Roughly, the two values 0 and 4096 (corresponding to a 12 bit value) represent −1.5 g and +1.5 g for high sensitivity setting (which we used here), whereby g is the earths acceleration (9.81m/sA2). For acceleration we set an interval (similar to the GPS interval) every 2 minutes to record 54 Bytes of acceleration with a sampling frequency of 10 Hz on the Z axis. This means the samples are not evenly spaced in time, instead the data are collected in "bursts". In our study, the acceleration sensor was turned on every 2 minutes for a certain time. This time was defined by the amount of data to be collected (which is user defined: here 54 Bytes) and the sampling frequency (also user defined: here 10 Hz). Since one axis was sampled, the sampling frequency per axis is full (here 10 Hz). One sampling point needs 1.5 Bytes, therefore the total amount of sampling points will be 54/1.5=36 i.e. 36/1=36 per axis. The total sampling time is 36/10 Hz=3.6 s. The next scheduled acceleration recording will be 2 min later (according to the interval). The required power is about 1 mA during acceleration recording.

Data Download and Initial Data Handling

We downloaded the stored data via an encrypted 868 MHz data download. During the download, a specific tag communicates with the handheld, battery powered base station exclusively and acknowledges and verifies the data packages that are being sent. Thus, all data are being transmitted fully and with perfect handshake recognition during the sending process. Once data are received by the base station, the base station acknowledges this receipt and programs the tag to erase this part of its memory. The base station records the data in a memory chip at a rate of ca. 1 Mb per minute. From each goat, we downloaded ca. 10 Mb of binary encoded data after 6 months of deployment of the tags. Data downloads stop after they are complete, which also means that all data on the tags are erased and the tags are ready to record new data for another 180 days, depending on the settings provided in the initial settings file.

Data from the base station are then directly transmitted to a computer from an SD memory chip card. The binary file can then either be transferred into a regular text file on a Windows PC, or uploaded directly to Movebank (www.movebank.org), where the data are unpacked and double-checked against duplicates. Furthermore, the observations are linked to the absolute time of recording as determined from the GPS module and the GPS location settings. Thus, the accuracy of timing measurements in the tags is given by the precision of the GPS time. Movebank stores the data in a relational data base with the main fields of animal identification number (ID), time, GPS location and movement, GPS error, acceleration, as well as reports on the technical properties of the tag (battery voltage, GPS time to fix, memory status etc.).

Data Inspection and Evaluation

Once data are in Movebank or on the PC computer, they can be visualized by linking the acceleration data to location data. The visualization is conducted by plotting acceleration values (as described above, as values between 0 and 4096) in time and linking it to geographical location as displayed either on N ASA Worldwind or on Google Earth (see FIG. 5). Thus, the researcher can simultaneously watch the behavior of the goats (acceleration in the Z axis) and their locations on the slopes of Mt. Etna.

The observations represent true timed samples of the goats' behavior (every 2 minutes for acceleration, every 30 minutes for GPS location), and as such are truly representative of the overall behavior of the goats. The acceleration behavior of the goats enables a quantitative determination of the movements of individuals in the Z-axis.

For the analysis of acceleration and thus behavior, we used the average values of the 36 acceleration measurements during a 3.6 second burst as well as their statistical variance. These average values were taken as quantitative indicators of the goats' activity during a sampling interval. We compared the acceleration values measured in this way between different times, e.g. hourly before a major volcanic event (see below) or afterwards. We present the cumulative sum of half hourly acceleration averages or acceleration variances over night as an indicator of the sensing of goats of environmental conditions. We also used the entire sum of nocturnal activity, measured as the cumulative average of acceleration values, to compare activity levels between nights (defined as the time between 20:00 h local time and 6:00 h local time).

To quantitatively analyze and compare the linear movements of goats during the day, we used the total daily distance travelled by goats from their nocturnal resting location to their evening resting location in a linear way to represent the unidirectional movements of goats during a day.

Volcanic Activity

We received official volcanological summary data from the Italian National Volcanological Institute (INGV) to characterize the magnitude of the volcanological events. The INGV runs at least 26 semi-automated measurement stations around Mt. Etna and also conducts visual observations and on-site chemical and geographical/geological measurements on Mt. Etna continuously. Measurements we used in our characterization of the overall magnitude of the volcanic event included the seismic activity of Mt. Etna as well as descriptions of the volcanological events such as the altitude of the volcanic eruption and the magnitude of material emitted during an event.

Based on these data we highlighted 9 volcanic events during the study period. Most of these events were minor in the sense that only small amounts of ash were emitted or only local lava fountains were seen that did not produce lava flows to the outside of the volcano. Thus, people and animals on the outskirts of the volcano were not visually affected by these events, and no tremors of earthquakes were felt by humans in the area of Randazzo. Only two events were characterized as 'major' during the current study period. The first one was the $19^{th}$ paroxysmal event starting as a major event in the morning hours of January 5 and lasting until approximately midday of that day, the second one was the $21^{st}$ paroxysmal event. Official descriptions of these events by the INGV are given below.

The 19th Paroxysmal Event (Based on Official Information Published by the INGV):

The 5 Jan. 2012 Paroxysmal Eruptive Episode at Etna's New Southeast Crater

Following a quiet interval of 50 days, the New Southeast Crater (New SEC) of Etna reactivated on the evening of 4 Jan. 2012, and produced the first paroxysmal eruptive episode of the year (the 19th since the beginning of the series initiated on 12 Jan. 2011) on the morning of 5 January. The photo in FIG. 1 shows the acme of this paroxysm, shortly after 06:00 GMT.

The reawakening was preceded by various signs of unrest recorded by the observation systems of the INGV-Osservatorio Etneo (INGV-OE) during the first few days of 2012; these included strong fluctuations in the volcanic tremor amplitude, an increase in degassing from the Bocca Nuova that culminated in an explosion quake accompanied by a minor emission of vapor and ash on the evening of 2 January, and finally by the resumption of weak explosive activity within the New SEC on 4 January. About 08:20 GMT on 4 January, small explosion signals started to be recorded by the EBELO infrasonic recorder, located about 0.9 km to the southeast of the crater.

On the late evening of 4 January weak incandescence was visible in correspondence with the New SEC; however, observations were strongly hampered by inclement weather. From 22:30 GMT Strombolian activity was observed intermittently by INGV-OE staff from various sites on the southeastern and northeastern flanks of the volcano, and from 02:00 GMT on 5 January the activity was under continuous observation. Around 02:45 GMT, a small lava flow began threading its path across the deep notch curring the southeastern crater rim; this flow advanced very slowly following the same path of the lava flows emitted during the previous paroxysmal episodes.

During the following hours, the Strombolian activity increased in intensity and from 04:00 GMT it increased more rapidly to become virtually continuous. Between 04:45 and 05:00 GMT, the Strombolian activity passed into discontinuous, pulsating fountaining generating jets 100-150 m high.

About 04:50 GMT, ash emission had become significant, and this was accompanied heavy fallout of scoriae, spatter, and bombs onto the flanks of the cone. From 05:15 GMT onward, lava fountaining was continuous, generating an eruption column of ash and vapor that rapidly rose in height, reaching an elevation of 7000-8000 m above the sea-level around 06:00 GMT (see FIG. 1).

During the time interval between 05:35 and 05:45 GMT, incandescent pyroclastics completely covered the cone, which interacting with snow began to form avalanches and small pyroclastic flows extending for a few hundred meters. These flows repeatedly pushed far into the snow cover at the base of the cone, provoking phreatomagmatic phenomena and small lahars (mud flows), in particular on the northeastern, eastern, and southern flanks of the cone. The longest flows nearly reached the central portion of the eruptive fissure of 13 May 2008.

The vents on the upper northern flank of the cone emitted a small lava flow that travelled a few hundred meters stopping before reaching the upper portion of the 13 May 2008 eruptive fissure.

Around 06:00 GMT, several eruptive vents activated along the fracture that cuts the northern rim of the New SEC cone, producing small intermittent lava fountains. At 06:20 GMT, a powerful explosion marked the opening of a vent on the upper southeast flank of the cone, destroying a portion of the southeastern crater rim.

Shortly after 06:30 GMT, the Bocca Nuova emitted a puff of ash, followed by weaker emissions of ash mixed with ash. At the New SEC, paroxysmal eruptive activity continued with full vigor until 06:57, and then terminated rather brusquely within the next few minutes. Only passive emission of ash continued after this until about 07:30 GMT at the New SEC, and lasted until 08:30 GMT at the Bocca Nuova.

This paroxysmal episode has occurred after one of the longest repose intervals of the current eruptive sequence initiated one year ago; only the intervals between episodes #2 (18 Feb. 2011) and #3 (10 Apr. 2011) and between episodes #4 (12 May 2011) and #5 (9 Jul. 2011) were longer −51 and 58 days, respectively. In terms of explosivity, this was one of the most violent events of the sequence, but the quantity of lava emitted was much inferior to that of previous episodes. The main lava flow toward southeast in the direction of the Valle del Bove, advanced little more than 2 km, flanking the northern side of the Serra Giannicola.

For a few tens of minutes following the cessation of the paroxysm, the entire northern flank of the New SEC cone showed a wholesale gravitational movement due to the slow sliding of the abundant pyroclastic material deposited on that side. This process was accompanied by the release of abundant bluish gas, but did not result in the formation of a rheomorphic flow.

The 21th Paroxysmal Event (Based on Official Information Published by the INGV):

The 4 Mar. 2012 paroxysmal eruptive episode appeared at Etna's New Southeast Crater. The third lava fountaining episode at the New Southeast Crater (New SEC) of Etna in this year—the 21st since the start of the current eruptive sequence—occurred on the morning of 4 Mar. 2012. This event was more violently explosive, generating small pyroclastic flows and lahars (mudflows), due to the explosive interaction between lava flows and thick snow cover on the terrain (see FIG. 1).

After the lava fountaining episode of 9 Feb. 2012, Etna remained quiescent for one week. On the morning of 16 February, small ash emissions resumed from the New SEC, and for 18 days, weak, sporadic Strombolian activity continued on the crater floor. Occasionally, faint glow was observed at night; there was also a conspicuous increase in the number of sources and in the volume of fumarolic emissions along the southern rim of the crater. During the last few days of February, this activity was accompanied by an increase of the explosive activity within the conduit of the Northeast Crater, producing loud bangs, which were well audible all over Etna's summit area. The volcanic unrest during the second half of February was accompanied by more accentuated fluctuations of the volcanic tremor.

During the early morning hours of 4 Mar. 2012, the volcanic tremor amplitude showed a rapid increase; at the same time, the Strombolian explosions within the crater became more frequent and more intense. Shortly after 06:00 GMT (local time −1), lava started to overflow through the deep breach that cuts the southeastern rim of the crater. The lava flow reached the southeastern base of the cone after about 15 minutes and from there advanced toward the western rim of the Valle del Bove. In the meantime, the explosive activity was continuously waxing, and passed into continuous lava fountaining with development of an eruption column about 07:30 GMT. The abundant fall of large-sized pyroclasts onto the steep flanks of the cone led to the formation of rock and dust avalanches; around 07:50 small pyroclastic flows were generated by the partial collapse of the eruption column. These flows descended mainly on the northeastern flank of the cone, and to some lesser degree on the south flank.

Also around 07:50 GMT, a lava flow was emitted from a new eruptive vent on the upper southwestern flank of the New SEC cone and started to descend in the saddle between the old and new SEC cones, interacting violently with thick snow covering the ground. This interaction provoked powerful explosions and small pyroclastic flows, the largest of which advanced rapidly across the flat terrain immediately to the east of the first eruptive fissure that opened on 17 Jul. 2001. Melting of the snow, in turn, led to the formation of a lahar, which descended toward the "Belvedere" monitoring station, on the western rim of the Valle del Bove, passing a few tens of meters to the north of the monitoring instruments.

During the phase of maximum intensity in the eruptive activity, a lava flow was also emitted from an eruptive fissure on the upper northern flank of the cone. This flow descended a few hundred meters toward northeast, surrounding the northern base of the cone. The main lava flow, which was fed across the breach in the southeastern rim of the crater, followed a nearly identical path to that of the lava flow emitted during the 9 February eruptive episode. After descending the steep western slope of the Valle del Bove, the flow split into several branches on the more gently sloping terrain at the base of the slope. These branches exceeded in length those of the 9 February flow, reaching a total distance of about 3.5 km from the crater.

The lava flow emitted from the fissure on the southwestern flank of the cone remained active for a few hours after the cessation of the paroxysmal activity, advancing slowly on the trace of the lahar that had occurred during the culminating events of 07:52 GMT.

The advance of the lava flows on thick snow cover was often accompanied by phreatic explosions, which generated violent jets of vapor and launched rock fragments to several tens of meters away; these phenomena were observed along the southern lava flow and along the main lava flow descending into the Valle del Bove.

Shortly after 09:00 GMT, the activity showed the first signs of diminishing in intensity; lava fountaining ceased at 09:32, two hours after the onset of the paroxysmal phase.

This episode occurred 24 days after the preceding one, of 9 Feb. 2012, and was considerably more violent. The eruption column reached a height of several kilometers above the summit of Etna. Ash and lapilli were carried by the wind toward northeast, affecting the areas around Piedimonte Etneo and Taormina. Fine ash fell as far as the Messina area and southern Calabria. Once more, the pyroclastic cone of the New SEC has grown in height, mainly on its northern rim.

Statistical Analysis

Data were analyzed using Movebank and SPSS (2011) for Windows. We present data as averages ±standard deviation, except where indicated.

EXAMPLE 2

Aberrant Nocturnal Activity of Goats in Anticipation of a Volcanic Event in the Morning We determined the nocturnal sum of the individual average acceleration variances for 8 goats during the 5 days leading up to a major volcanic event, during the night before the major volcanic event, and for 5 days after the major volcanic event. The data show a clear peak in the sum of average individual acceleration variances per night in anticipation of the major volcanic event (see FIG. 7A).

For the prediction of a major volcanic activity, we suggest observers should use the doubling of the sum of acceleration variances above the 10-day population average.

In contrast to a major volcanic event (as defined above), we did not find any significant aberrant nocturnal behavior of the goats during a minor event.

Time Course of Aberrant Nocturnal Activity of Goats in Anticipation of a Volcanic Event To understand the temporal scale of predictability of a major volcanic event, we used the accumulation curve of average goat activity, measured as acceleration in the z-axis, during control nights preceding the major volcanic event. We compared these accumulation curves to the curve during the night before a major volcanic event.

We found that approximate 5 hours before the major volcanic event, the average acceleration behavior of goats significantly increased above background levels (see FIG. 8).

More specifically, the average acceleration behaviour of goats per night was plotted against time as an acceleration curve, i.e., adding all average acceleration values together over time (see FIG. 8). During control nights, there is a slow but constant accumulation of average acceleration behaviour. Only during the night with a major volcanic activity there existed a sudden increase in the accumulation of average acceleration behaviour. The slope of the accumulation curve remained steeper after the sudden increase, compared to control nights.

For the prediction of a major volcanic activity, we suggest observers should use a more than 30% increase in the nocturnal accumulation curves of average acceleration behavior of goats. In contrast to a major volcanic event, we did not find any significant aberrant nocturnal accumulation of average acceleration behavior of the goats during a minor event.

Linear Daily Movement as Predictor of Major Volcanic Activity

To understand whether one could predict a major volcanic event from the diurnal behavior of animals, we determined the sum of daily uni-directional location movements of 8 goats (see FIGS. 9A and B).

For the prediction of a major volcanic activity, we suggest observers should use the doubling of the daily unidirectional movements of a population of goats above the 10-day population average.

In contrast to a major volcanic event, we did not find any significant aberrant daily unidirectional movements of the goats during a minor event.

EXAMPLE 3

Forecasting Volcanic Events by Using a Mixed Population of Animals

Data over one year from 9 goats and 4 sheep at Mount Etna in Sicily, Italy have been gathered. The study site continued to be the northern flanks of Mt. Etna upwards from the small town of Randazzo. Exactly the same methods as described herein above have been used.

Mt. Etna was seismically and volcanically active during the period of measurement. As in the foregoing Examples, the volcanic events have been classified into "major" and "minor" events. "Major" events consisting of volcanic eruptions with tephra stones thrown high into the atmosphere and ash clouds rising up to several kilometers. "Minor" events are those that only showed eruptions rising into low altitudes of a few 100 meters above the peak of Mt. Etna or volcanic eruptions that only occurred within the crater of Mt. Etna. In particular, during minor events only small amounts of ashes are emitted or only local lava fountains occur that did not produce lava flowing to the outside of the volcano (Volcanic Explosivity Index (VEI) of 1). Although minor events are volcanically significant, they do not comprise any danger to the lives of animals living along the slopes of Mt. Etna. Even major events most likely do not kill or harm animals, but could at least become very unpleasant for them, e.g. when hot tephra stones or acidic ash are falling down upon them.

The classification into "major" and "minor" events has been confirmed by human visual and acoustical observation. In particular, a paroxysm occurred on Apr. 27, 2013. During the data readout during the paroxysm of Apr. 27, 2013, human witnesses observed the lava eruption and explosion. While reading out the data from the goats in Randazzo, black ash clouds rise from the volcanic caldera. No behavioral changes in the goats and sheep have been detected before or during the paroxysm. Based on the pre-set classification scheme described herein, the paroxysm of Apr. 27, 2013 has been classified as a "minor event".

TABLE 1

Major events that occurred

| Date of the major event | Time of the major event | Time when the threshold triggered an alert/notification |
|---|---|---|
| Apr. 12, 2012 | 14:30 | 11:15 |
| Apr. 24, 2012 | 1:40 | 22:25(on Apr. 23, 2012) |
| Feb. 19, 2013 | 4:10 | 23:20(on Feb. 18, 2013) |
| Mar. 5, 2013 | 23:12 | 20:55 |
| Mar. 16, 2013 | 17:00 | 14:15 |

Similar to the previous major events (that were part of Example 2), the 5 additional major events were predicted by the behavior of the 9 goats and 4 sheep ahead of time. The alert thresholds set forward herein were used in the additional events as well, and thus comprise general alert thresholds for disaster forecast (e.g., when larger vertebrates are used).

Again, unidirectional movement during the daytime events and 3D-acceleration-triggered activity events at night were used as described herein. In particular, the threshold value has been determined as follows.

The threshold value was the double average value of the summated daytime-integrated unidirectional movement of the population. Accordingly, the test profile was generated in the same manner: the unidirectional movement of each animal was integrated over the whole day and daytime-integrated unidirectional movements of the test night of each animal of the population were added. Thus the alert was set, if the ratio between the test profile and the reference profile was 2, according to the aforementioned threshold.

The threshold value was the double average value of the summated overnight-integrated activity of the population. Accordingly, the test profile was generated in the same manner: the activity of each animal was integrated over the whole night and the overnight-integrated activities of the test night of each animal of the population were added. Thus the alert was set, if the ratio between the test profile and the reference profile was 2, according to the aforementioned threshold.

Compared to the volcanic events, low earthquake activity (i.e. seismic events below 5 on the Richter magnitude scale) at Mt. Etna did not allow for any predictions of volcanic activity. As shown in FIG. 14, seismic activity at Mt. Etna is quasi continuous, with few major events above category 4 on the Richter magnitude scale. These events do not coincide with the volcanic events as determined in FIG. 13 13. The goats and sheep did not react to or anticipate low seismic events (i.e. seismic events below 5 on the Richter magnitude scale), as expected because these events do not pose any threat nor are the highly visible for humans. As the population of animals did not forecast low seismic events (i.e. seismic events below 5 on the Richter magnitude scale), false-positive alerts were prevented.

In summary, these data confirm that the described method and threshold can be used to predict major volcanic events at Mt. Etna, and potentially at other active volcanoes around the world, as well as potentially other natural disasters.

Conclusion

By using remote sensing of behavior via 3D-acceleration and GPS location logging, and transmitting data via VHF telemetry, we showed that feral goats and/or a mixed population of animals on Mount Etna, Sicily, actively engage in behaviors that allow for the remote prediction of major volcanological events.

The invention claimed is:

1. A method for use in forecasting an environmental event or a type of the environmental event, comprising:
    a. acquiring, by using a sensor unit, at least one test data set comprising a Z-axis acceleration data of at least one behavioural parameter of a population of animals, the sensor unit comprising a 3D-acceleration sensor configured to provide the Z-axis acceleration data;
    b. generating a test profile based on the at least one test data set, representing a behaviour status of the population of animals;
    c. calculating a ratio between the test profile and a first reference profile; and
    d. setting an alert, when the ratio reaches a predefined threshold value,
   wherein the at least one test data set further comprises location data indicating a geographical location of the population of animals,
   the method further comprising linking the Z-axis acceleration data with corresponding location data according to a recording time, and simultaneously displaying the Z-axis acceleration data and the location data on a map.

2. The method of claim 1, further comprising:
    a. acquiring at least one first data set of the at least one behavioural parameter of the population of animals in an absence of the type of the environmental event; and
    b. generating the first reference profile based on the at least one first data set, representing a normal behaviour status of the population of animals.

3. The method of claim 1 wherein the type of the environmental event is at least one event from among an earthquake, a marine earthquake, a tsunami, and a volcanic event.

4. The method of claim 1 wherein the population of animals comprises at least one of feral animals, semi-domestic animals, domestic animals, and animals in zoos.

5. The method of claim 1 wherein the population of animals comprises at least one of land animals, aquatic animals, and aerial animals.

6. The method of claim 1 wherein the population of animals comprises animals of the same species.

7. The method of claim 1 wherein the animals comprise at least one of goats, sheep, elephants, dogs, donkeys, monkeys, apes, and frogs.

8. The method of claim 1 wherein the population of animals comprises at least 5 animals.

9. The method of claim 1 wherein the at least one acquired behavioural parameter further comprises at least one of 3D-acceleration activity, and diurnal unidirectional movement.

10. The method of claim 1 wherein the predefined threshold value is a ratio of 2.

11. The method of claim 1 wherein the predefined threshold value is a ratio of 1.3.

12. The method of claim 1 further comprising:
    a. acquiring at least one second data set of the at least one behavioural parameter of the population of animals in a presence of the type of the environmental event; and b. generating a second reference profile based on the at least one second data set, representing an abnormal behaviour status of the population of animals.

13. The method of claim 12 wherein the presence of the environmental event is detected using methods comprising at least one of visual observation, acoustical observation, and seismological measurement.

14. The method of claim 12 wherein the predefined threshold value for raising the alert is determined using the first reference profile and the second reference profile.

15. The method of claim 1 wherein the alert is raised at least 2 hours prior to the environmental event.

16. A non-transitory computer program product comprising one or more computer non-transitory computer readable media having computer executable instructions for performing the method of claim 1.

17. The method of claim 1, wherein the at least one behavioural parameter comprising a nocturnal activity.

18. A system, for forecasting a type of an environmental event, comprising:
   a. a data acquisition unit configured to acquire at least one data set comprising a Z-axis acceleration data of at least one behavioural parameter of a population of animals;
   b. a profile generation unit configured to generate: at least one first reference profile, and at least one test profile, each based on the at least one data set;
   c. a ratio calculation unit configured to calculate a ratio between the at least one test profile and the at least one first reference profile; and
   d. an alert unit configured to raise an alert when the calculated ratio reaches a predefined threshold value,
   wherein the at least one test data set further comprises location data indicating a geographical location of the population of animals, and
   wherein the profile generation unit is further configured to link the Z-axis acceleration data with corresponding location data according to a recording time, and cause the Z-axis acceleration data and the location data to be simultaneously displayed on a map.

19. The system of claim 18 wherein: the profile generation unit is further configured to generate a second reference profile base on the at least one data set, and wherein the ratio calculation unit is further configured to determine the predefined threshold value based a ratio between the second reference profile and the at least one first reference profile.

20. The system of claim 18 wherein the data acquisition unit comprises a fixing unit configured to attach the data acquisition unit to an animal of the population of animals.

21. The system of claim 20 wherein the fixing unit is a neck collar.

22. The system of claim 18 wherein the data acquisition unit comprises a sensor unit, the sensor unit comprising a global positioning system receiver configured to generate location coordinates.

23. The system of claim 22 wherein the sensor unit is further configured to measure at least one physiological parameter of an animal of the population of animals using at least one of an electrocardiograph, an electroencephalograph, a clinical thermometer, an endocrinological measurement device, and an electromyograph.

24. The system of claim 18 wherein the data acquisition unit comprises at least one of a data memory unit and a data transmission unit.

25. The system of claim 24 wherein the data transmission unit comprises a VHF transceiver configured to transmit the at least one of the acquired at least one data set, the at least one generated profile, and the calculated ratio to a remote server unit.

26. The system of claim 18 wherein the data acquisition unit comprises a power supply.

27. The system of claim 26 wherein the power supply comprises at least one of a battery, a rechargeable battery, and a solar cell.

28. The system of claim 18 further comprising a remote server unit having at least one of a data memory unit, the profile generation unit, the ratio calculation unit, and the alert unit.

* * * * *